US010648936B2

(12) United States Patent
Hayashi et al.

(10) Patent No.: US 10,648,936 B2
(45) Date of Patent: May 12, 2020

(54) BLOOD CONDITION ANALYZING DEVICE, BLOOD CONDITION ANALYZING SYSTEM, BLOOD CONDITON ANALYZING METHOD, AND BLOOD CONDITION ANALYZING PROGRAM FOR CAUSING COMPUTER TO EXECUTE THE METHOD

(71) Applicant: Sony Corporation, Tokyo (JP)

(72) Inventors: Yoshihito Hayashi, Tokyo (JP); Marcaurele Brun, Tokyo (JP); Yoichi Katsumoto, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/772,550

(22) PCT Filed: Feb. 20, 2014

(86) PCT No.: PCT/JP2014/053997
§ 371 (c)(1),
(2) Date: Sep. 3, 2015

(87) PCT Pub. No.: WO2014/141844
PCT Pub. Date: Sep. 18, 2014

(65) Prior Publication Data
US 2016/0018346 A1 Jan. 21, 2016

(30) Foreign Application Priority Data

Mar. 15, 2013 (JP) ................... 2013-052664

(51) Int. Cl.
G01N 27/00 (2006.01)
G01N 27/02 (2006.01)
G01N 33/49 (2006.01)
G01N 27/22 (2006.01)
G01N 15/05 (2006.01)

(52) U.S. Cl.
CPC ............ G01N 27/02 (2013.01); G01N 15/05 (2013.01); G01N 27/221 (2013.01); G01N 33/49 (2013.01); G01N 2015/055 (2013.01); G01N 2333/805 (2013.01)

(58) Field of Classification Search
CPC .................. G01N 33/76; B01L 2400/0406
USPC .................... 422/50; 436/520, 521
See application file for complete search history.

(56) References Cited

U.S. PATENT DOCUMENTS

| 4,352,557 | A | * | 10/1982 | Schmid-Schonbein ...................... G01N 15/05 356/39 |
| 5,686,309 | A | | 11/1997 | Frank et al. |
| 6,128,518 | A | * | 10/2000 | Billings ............... A61B 5/0537 600/345 |
| 8,132,446 | B2 | | 3/2012 | Hayashi |
| 8,478,546 | B2 | | 7/2013 | Katsumoto et al. |
| 9,097,635 | B2 | | 8/2015 | Hayashi |
| 9,915,599 | B2 | | 3/2018 | Brun et al. |
| 9,952,168 | B2 | | 4/2018 | Brun et al. |
| 10,234,469 | B2 | | 3/2019 | Hayashi et al. |
| 10,393,761 | B2 | | 8/2019 | Hayashi et al. |
| 2004/0147032 | A1 | | 7/2004 | Martin et al. |
| 2009/0293595 | A1 | | 12/2009 | Hayashi |
| 2010/0136606 | A1 | | 6/2010 | Katsumoto et al. |
| 2011/0303556 | A1 | * | 12/2011 | Chen ................. G01N 33/4905 205/792 |
| 2012/0035450 | A1 | * | 2/2012 | Hayashi ............ G01N 33/4905 600/369 |
| 2012/0137753 | A1 | | 6/2012 | Hayashi |
| 2015/0323480 | A1 | | 11/2015 | Brun et al. |
| 2015/0346125 | A1 | | 12/2015 | Hayashi et al. |
| 2015/0377763 | A1 | | 12/2015 | Brun et al. |
| 2016/0011170 | A1 | | 1/2016 | Brun et al. |
| 2016/0025610 | A1 | | 1/2016 | Katsumoto et al. |
| 2016/0282366 | A1 | | 9/2016 | Hayashi et al. |
| 2016/0299124 | A1 | | 10/2016 | Brun et al. |
| 2017/0023597 | A1 | | 1/2017 | Hayashi et al. |
| 2017/0030934 | A1 | | 2/2017 | Hayashi et al. |
| 2018/0202955 | A1 | | 7/2018 | Brun et al. |

FOREIGN PATENT DOCUMENTS

| EP | 0 874 983 A1 | 11/1998 |
| EP | 2 375 244 A1 | 10/2011 |
| EP | 2 500 726 A1 | 9/2012 |
| JP | 03-099254 A | 4/1991 |
| JP | 2000-503772 A | 3/2000 |
| JP | 2010-181400 A | 8/2010 |
| JP | 2011-112497 A | 6/2011 |
| WO | WO 97/26528 | 7/1997 |
| WO | WO 97/26528 A1 | 7/1997 |
| WO | WO 2014/141844 A1 | 9/2014 |

OTHER PUBLICATIONS

Treo et al., Hematocrit measurement by dielectric spectroscopy, Proceedings of the Second Joint EMBS/BMES Conference, Oct. 23-26, 2002, pp. 1750-1751.

Japanese Office Action dated Sep. 10, 2019 in connection with Japanese Application No. 2018-194805, and English translation thereof.

Iriko et al., Erythrocyte Agglutination (Rouleaux Formation). Biological Engineering. 2000, vol. 78(5); pp. 162-165.

Beving et al., Dielectric properties of human blood and erythrocytes at radio frequencies (0.2-10 MHz); dependence on cell volume fraction and medium composition, Eur Biophys J, Jan. 1, 1994, vol. 23, pp. 207-215.

(Continued)

Primary Examiner — Natalia Levkovich
(74) Attorney, Agent, or Firm — Wolf, Greenfield & Sacks, P.C.

(57) ABSTRACT

There is provided a blood condition analyzing device including an erythrocyte quantitative evaluation unit configured to evaluate a hematocrit value and/or a hemoglobin amount on the basis of an electrical characteristic of a blood sample at a frequency of 2 to 25 MHz.

15 Claims, 28 Drawing Sheets

(56) References Cited

OTHER PUBLICATIONS

Pribush et al., Dielectric approach to investigation of erythrocyte aggregation. II. Kinetics of erythrocyte aggregation-disaggregation in quiescent and flowing blood, Biorheology, vol. 37, Jan. 1, 2000, pp. 429-441.
Pribush et al., Dielectric approach to the investigation of erythrocyte aggregation: I. Experimental basis of the method, Biorheology vol. 36, Jan. 1, 1999, pp. 411-423.
International Search Report and Written Opinion and English translation thereof dated Mar. 25, 2014 in connection with International Application No. PCT/JP2014/053997.
International Preliminary Report on Patentability and English translation thereof dated Sep. 24, 2015 in connection with International Application No. PCT/JP2014/053997.
Partial European Search Report dated Sep. 27, 2016 in connection with European Application No. EP 14763083.4.
Extended European Search Report dated Jan. 20, 2017 in connection with European Application No. 14763083.4.
Chinese Office Action dated Feb. 28, 2017 in connection with Chinese Application No. 201480012889.3 and English translation thereof.
Japanese Office Action dated Mar. 13, 2018 in connection with Japanese Application No. Japanese 2015-505350 and English translation thereof.
Irimajiri et al., Red Blood Cell Agglutination from Standpoint of Dielectric Behavior of Whole Blood (Formation of Nummular Massages), [Zenketsu no yuden kyodo kara mita sekkekkyu gyoshu (Renzen Keisei)], Biological Engineering, 2000, vol. 78, No. 5, pp. 162-165.
Fabry, Mechanism of erythrocyte aggregation and sedimentation. Blood , vol. 70, No. 5 (Nov.), 1987:pp. 1572-1576.
Hayashi et al., The effects of erythrocyte deformability upon hematocrit assessed by the conductance method. Physics in Medicine and Biology, vol. 54, 2009: pp. 2395-2405.
Irimajiri et al., Rapid Report—Dielectric monitoring of rouleaux formation in human whole blood: a feasibility study. Biochimica et Biophysica Acta , vol. 1290, 1996: pp. 207-209.
Irimajiri et al., Zenketsu no yuden kyodo kara mita sekkekkyu gyoshu (Renzen Keisei). Biotechnology, vol. 78, No. 5, 2000: pp. 162-165.
Chinese Office Action dated Sep. 29, 2017 in connection with Chine Application No. 201480012889.3 and English translation thereof.
Treo et al., Hematocrit Measurement by Dielectric Spectroscopy, IEEE Transactions on Biomedical Engineering, Jan. 2005, vol. 52, No. 1, pp. 124-127.

\* cited by examiner

FIG. 4
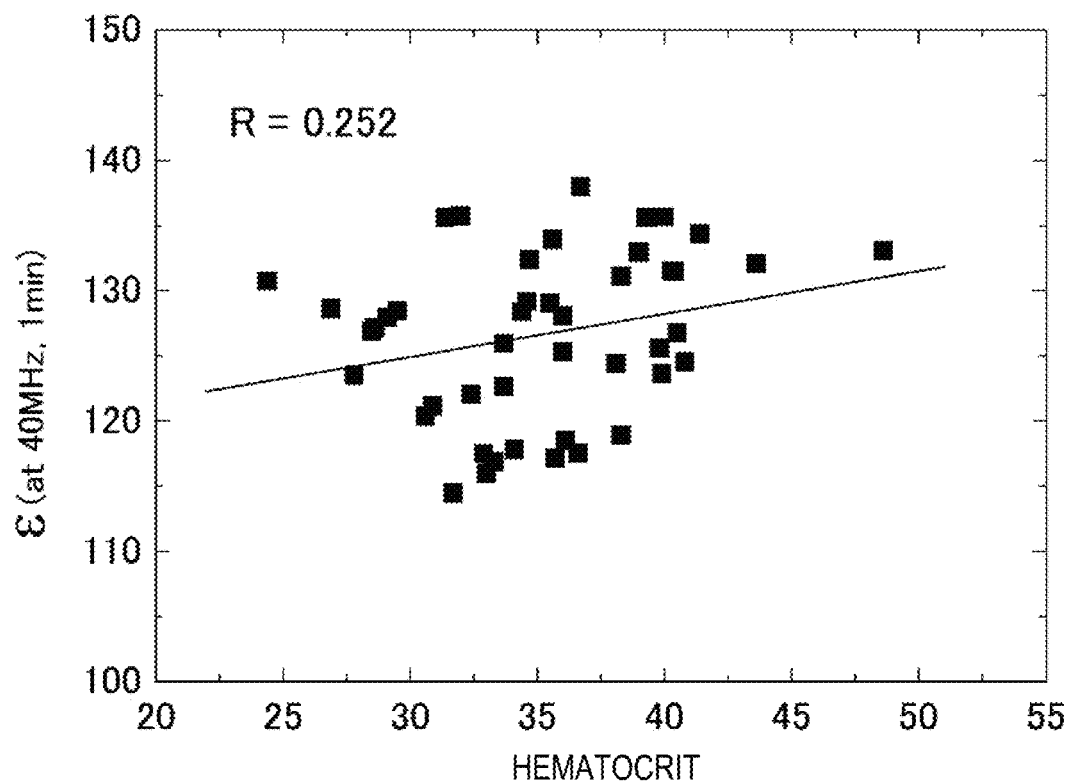
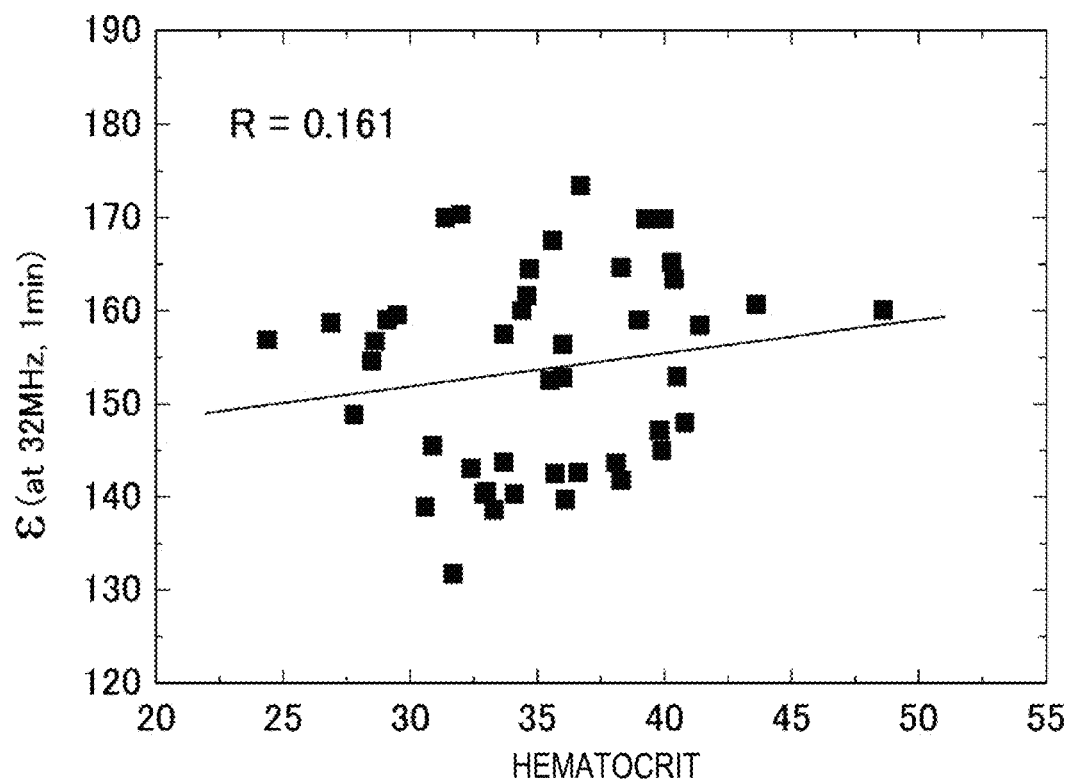

FIG. 5
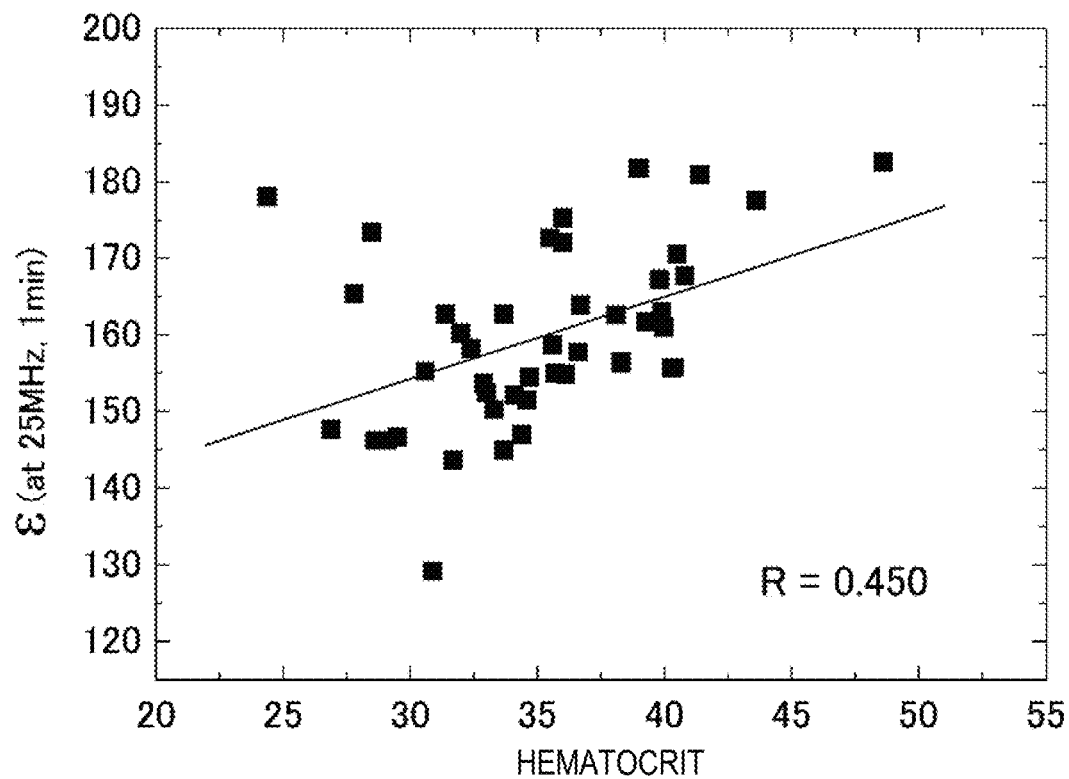
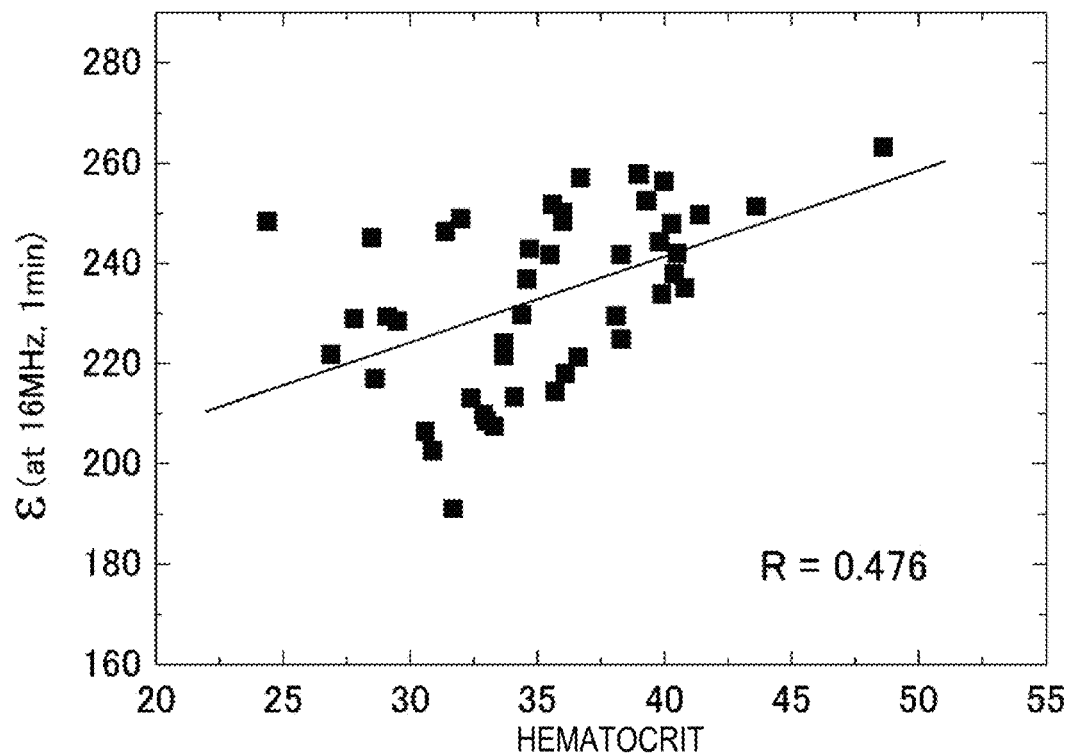

FIG. 6
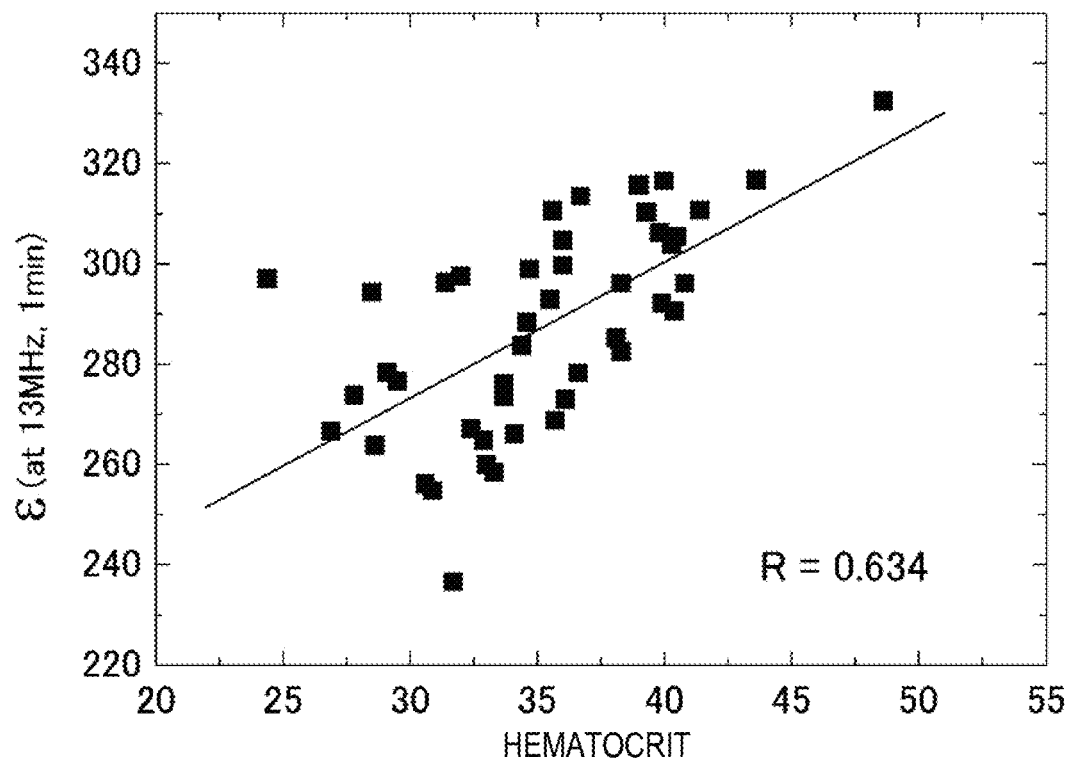
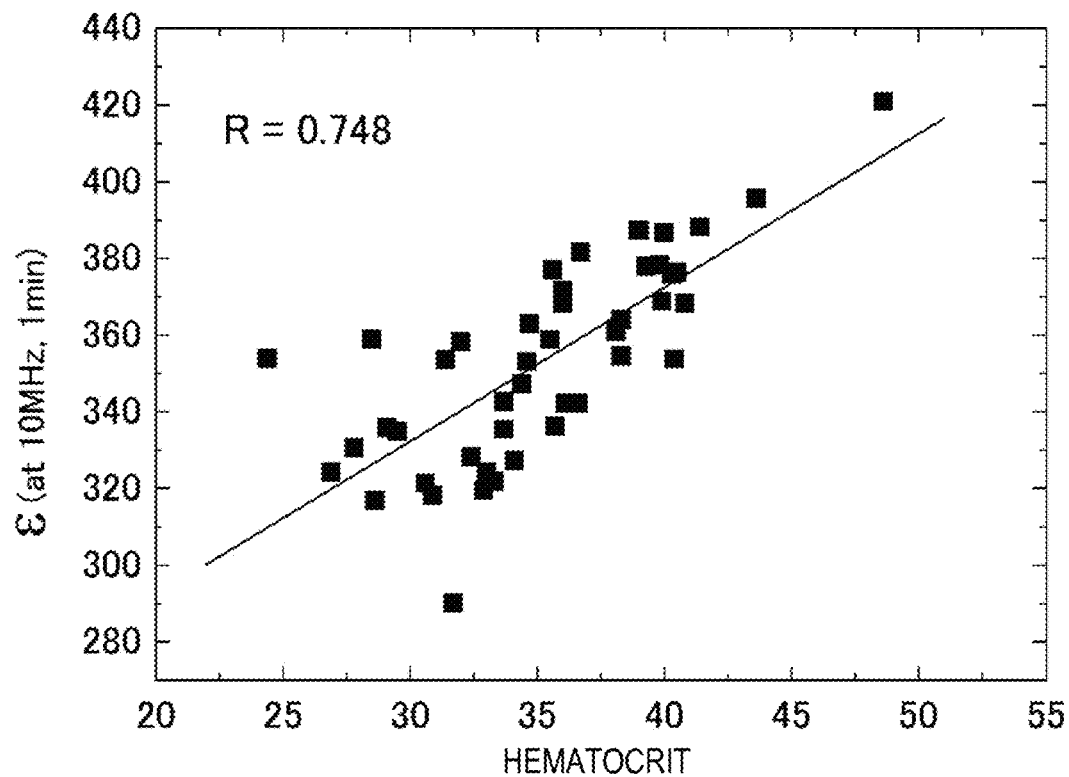

FIG. 7
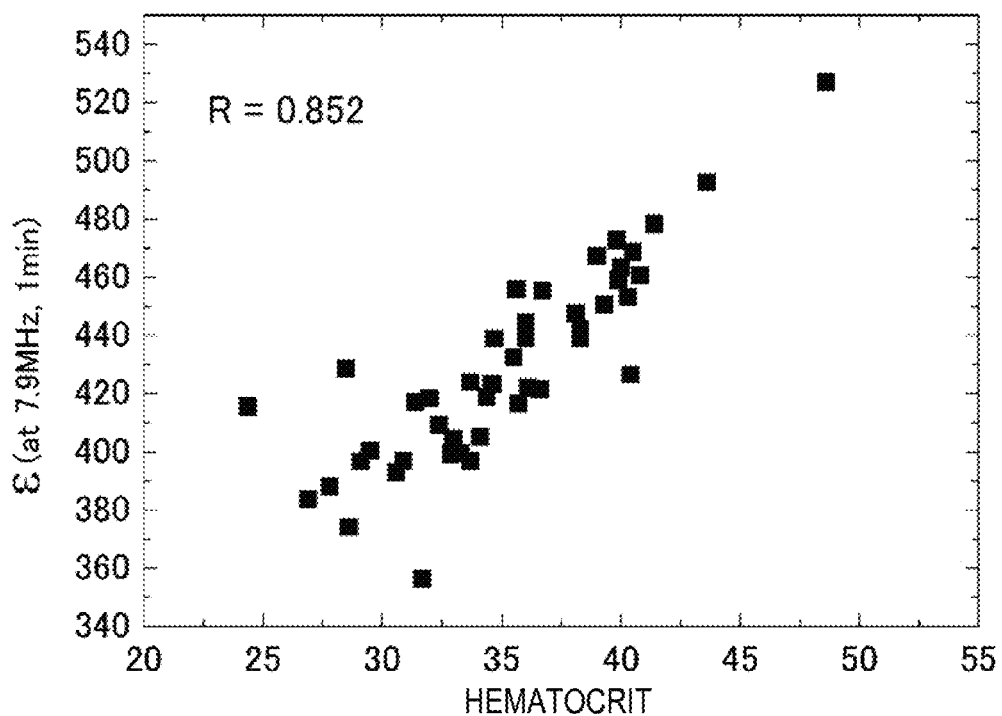
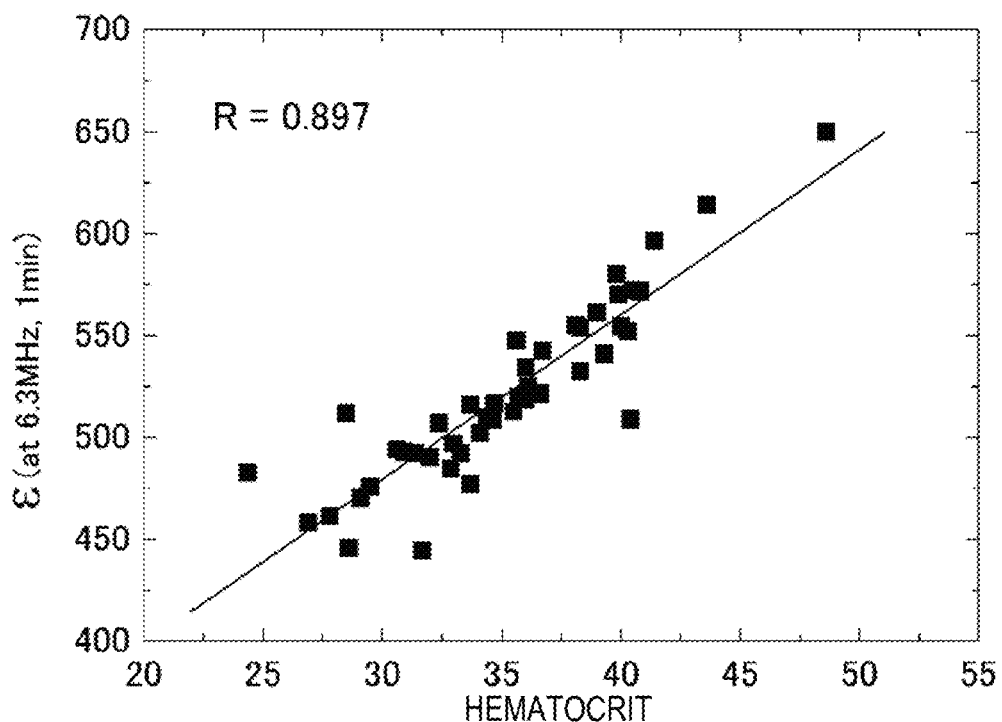

FIG. 8
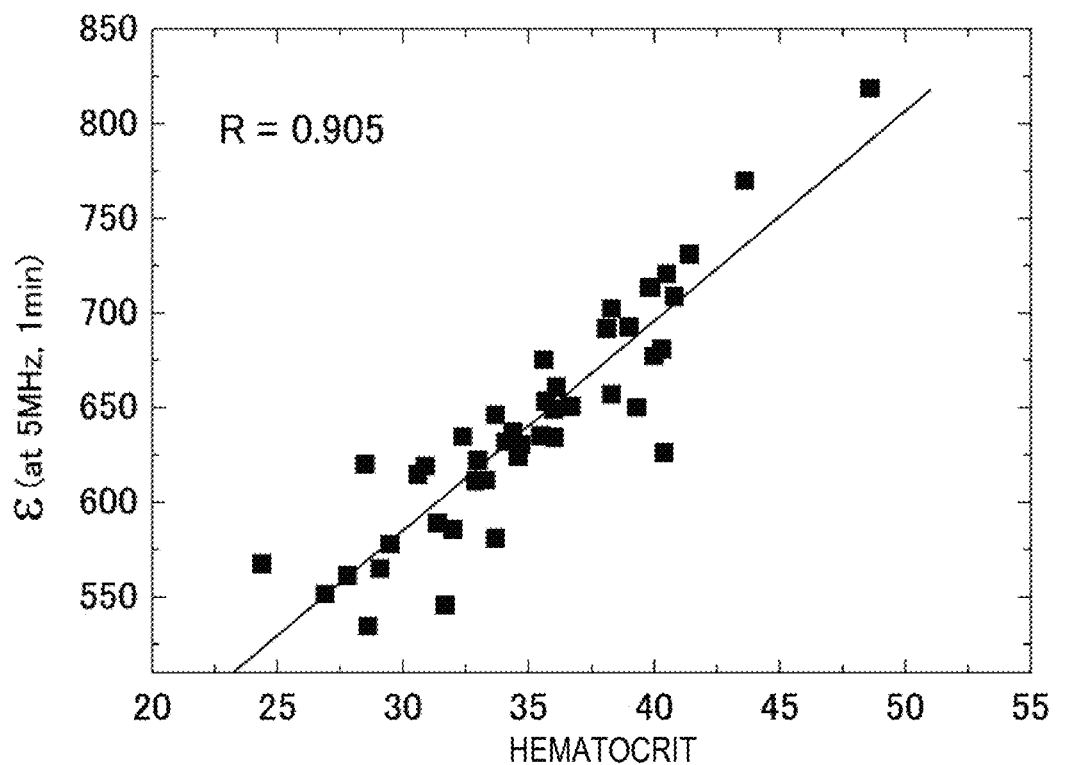
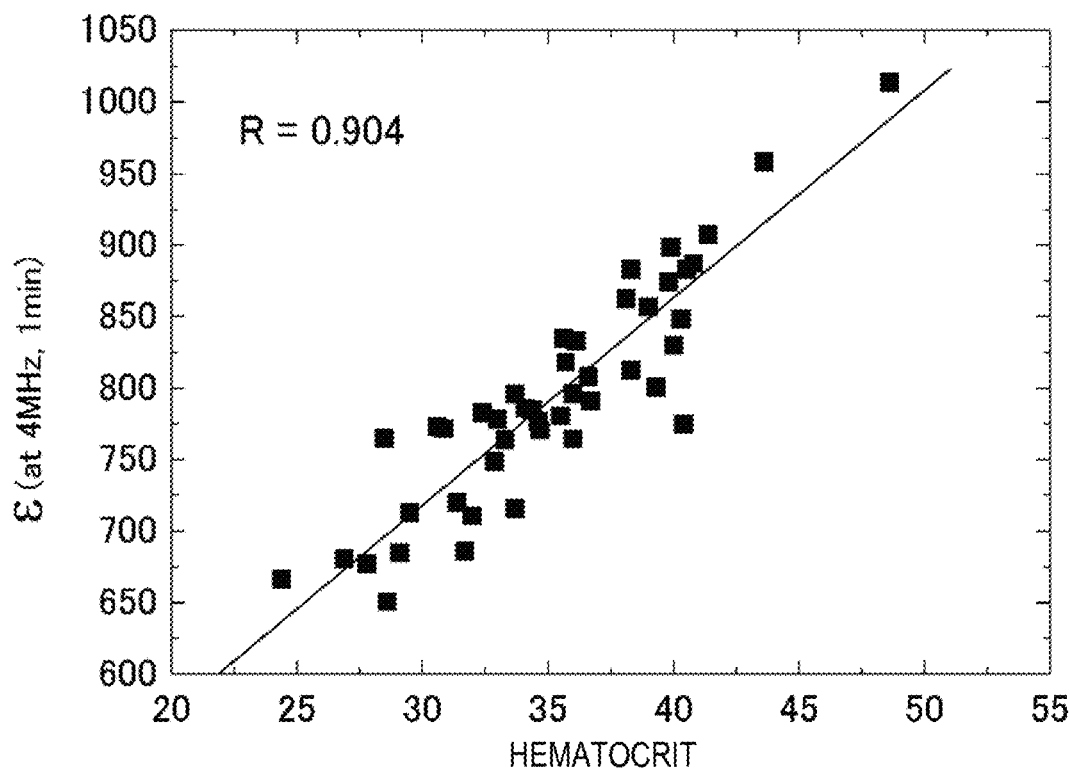

FIG. 9
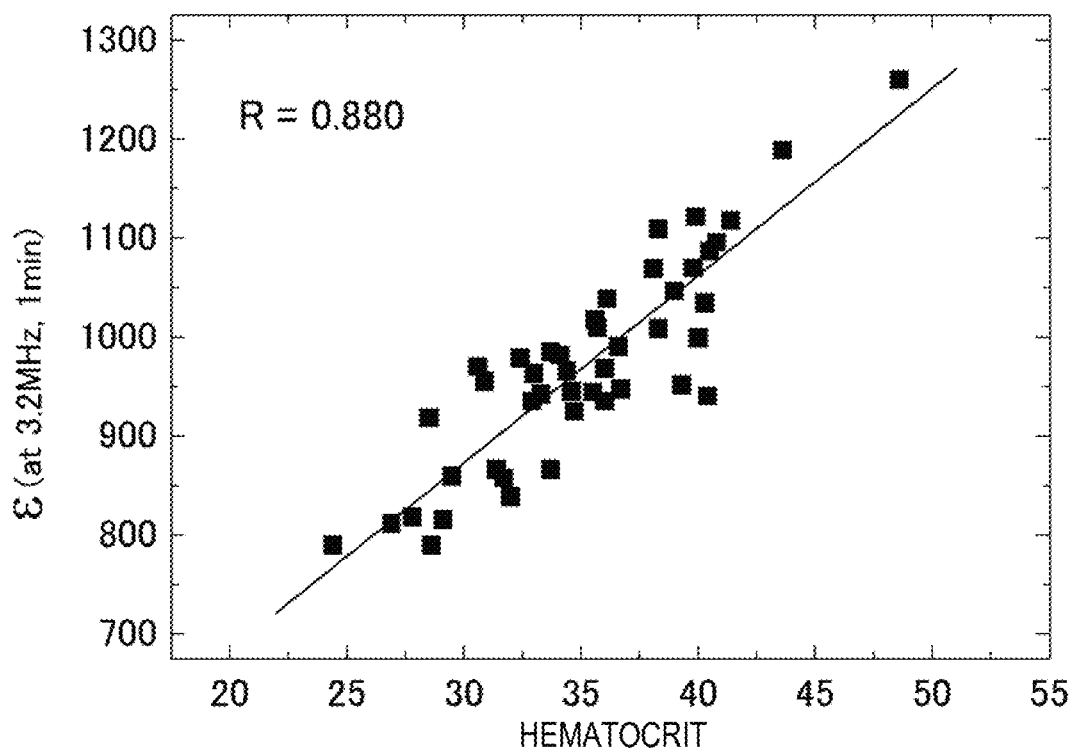
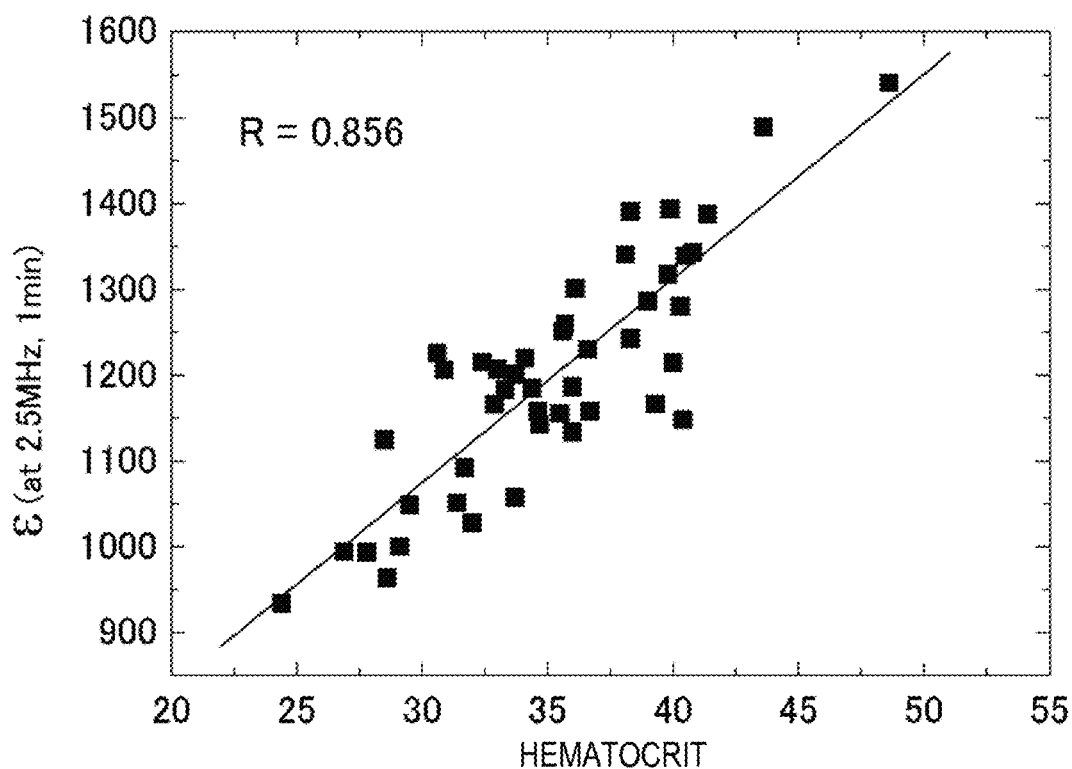

FIG. 11
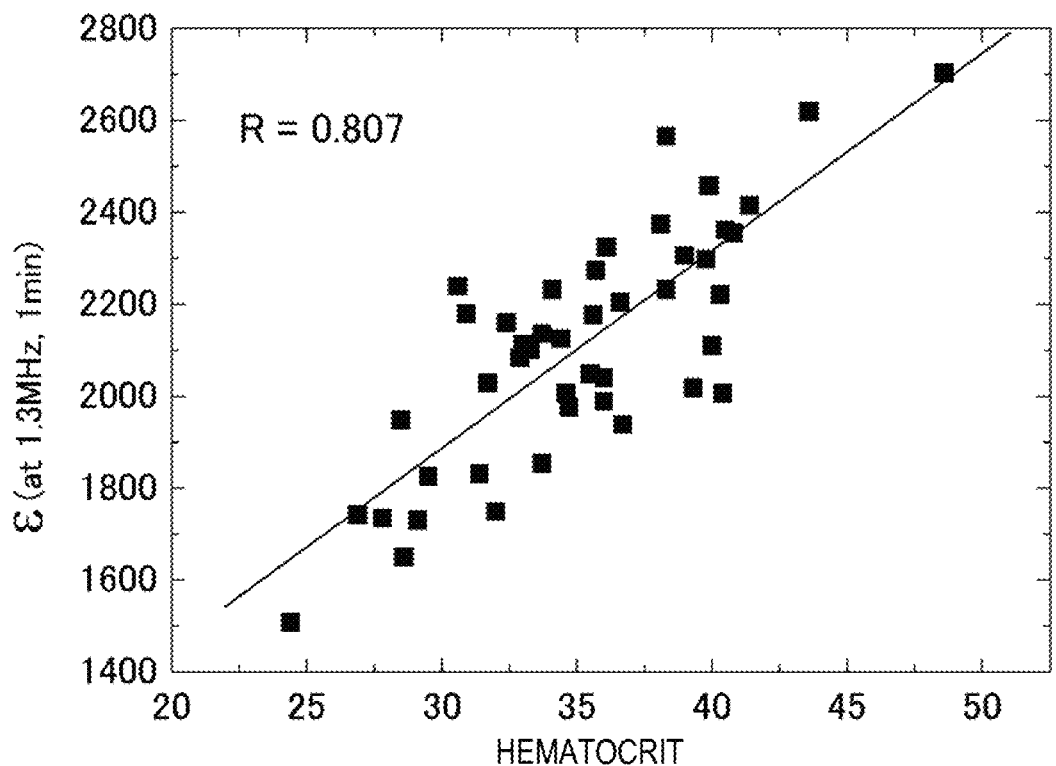
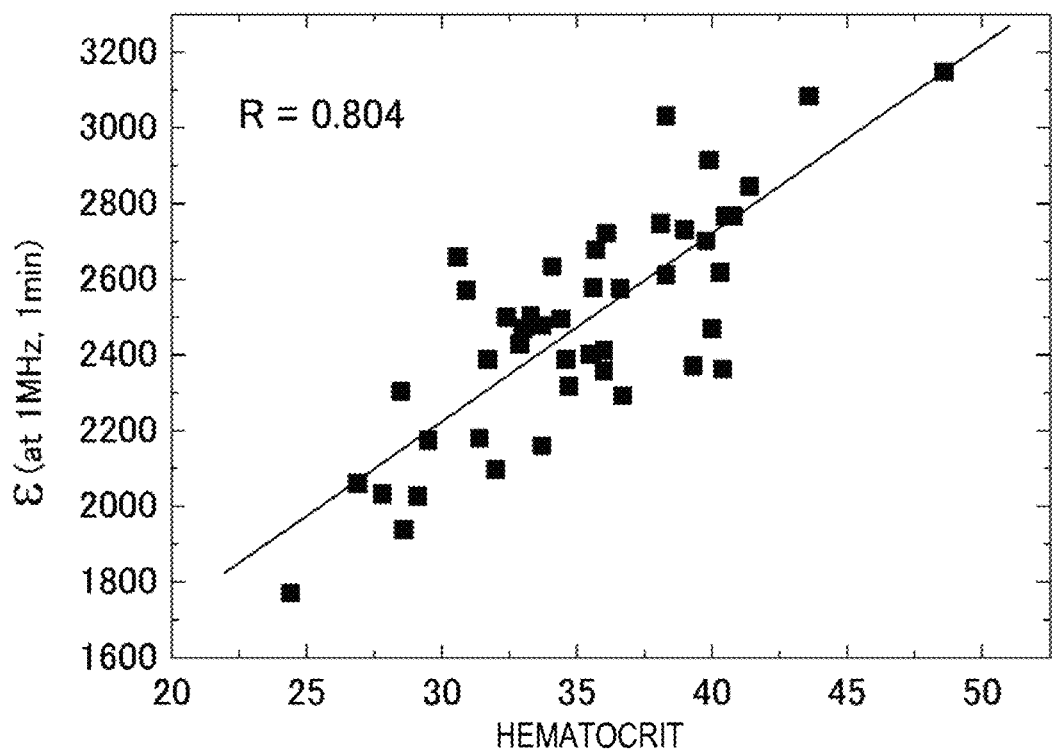

FIG. 13
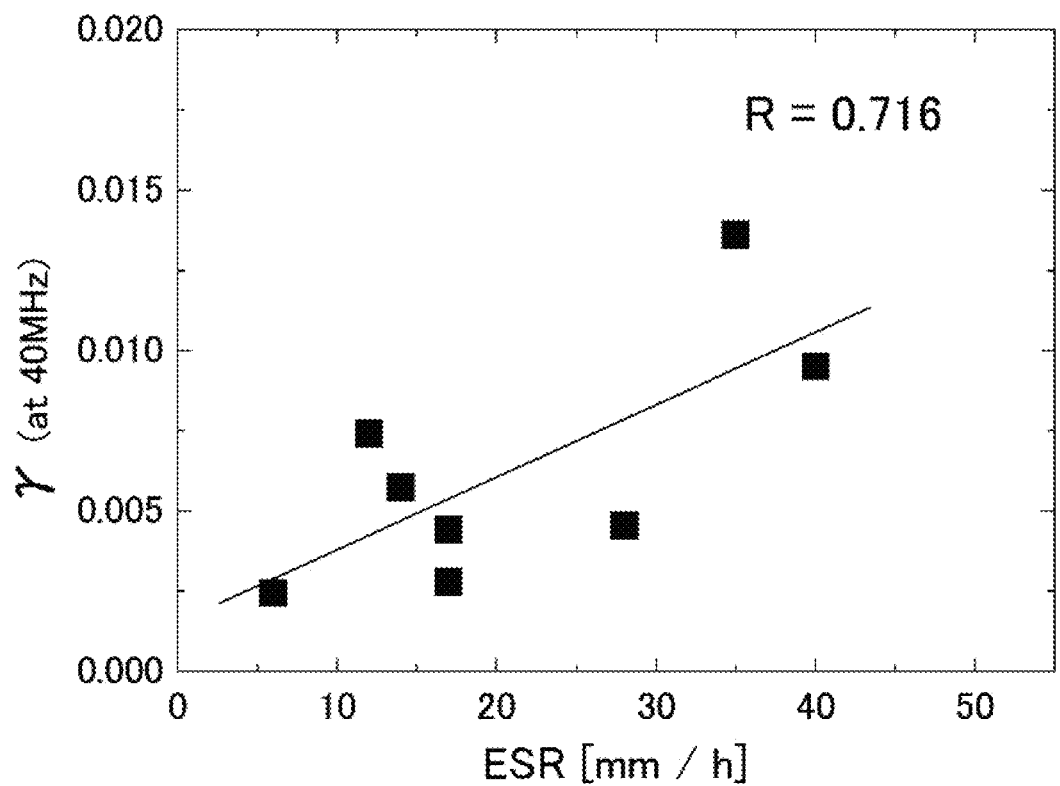
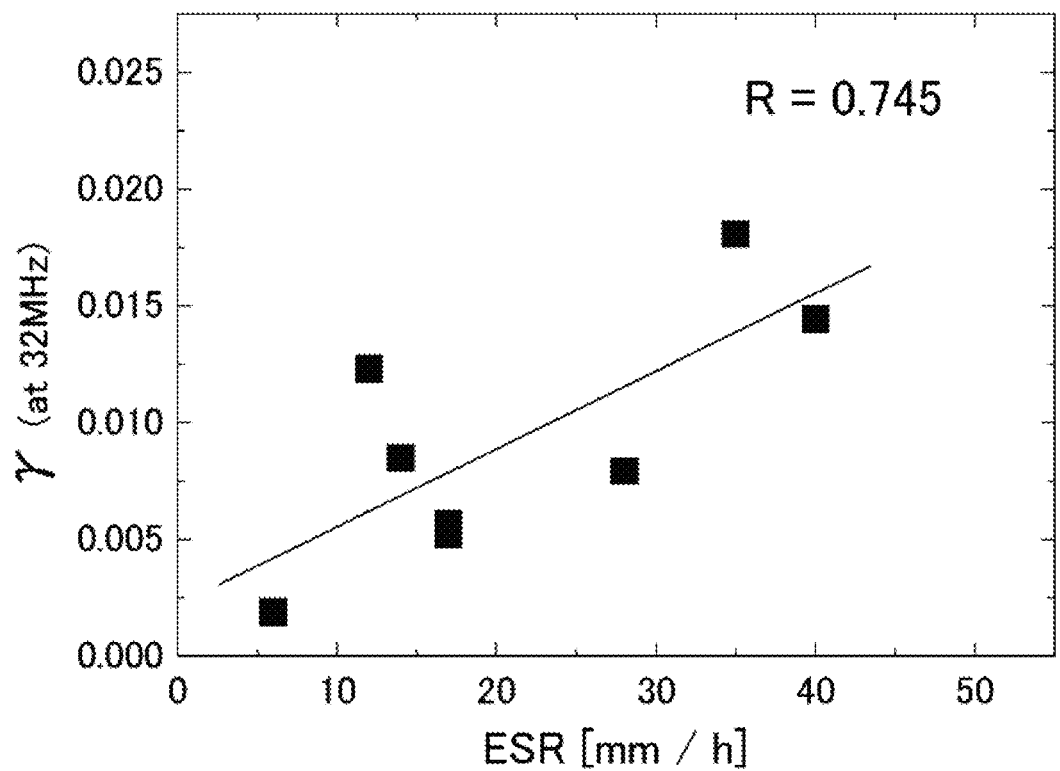

FIG. 14
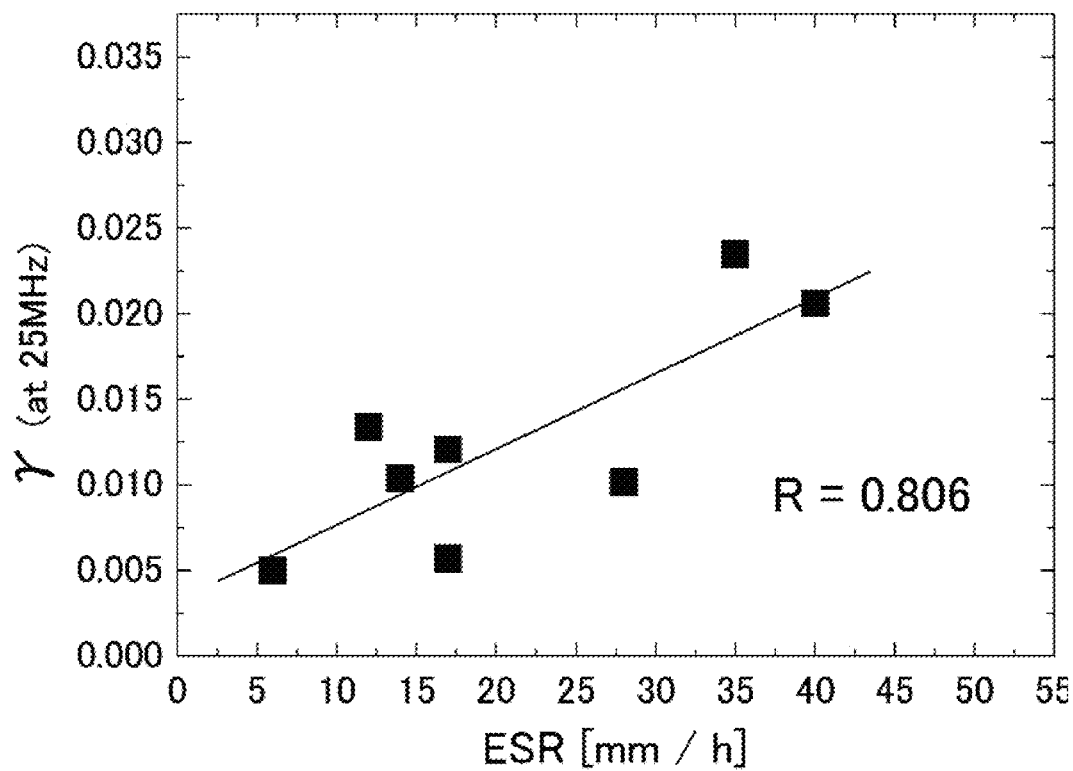
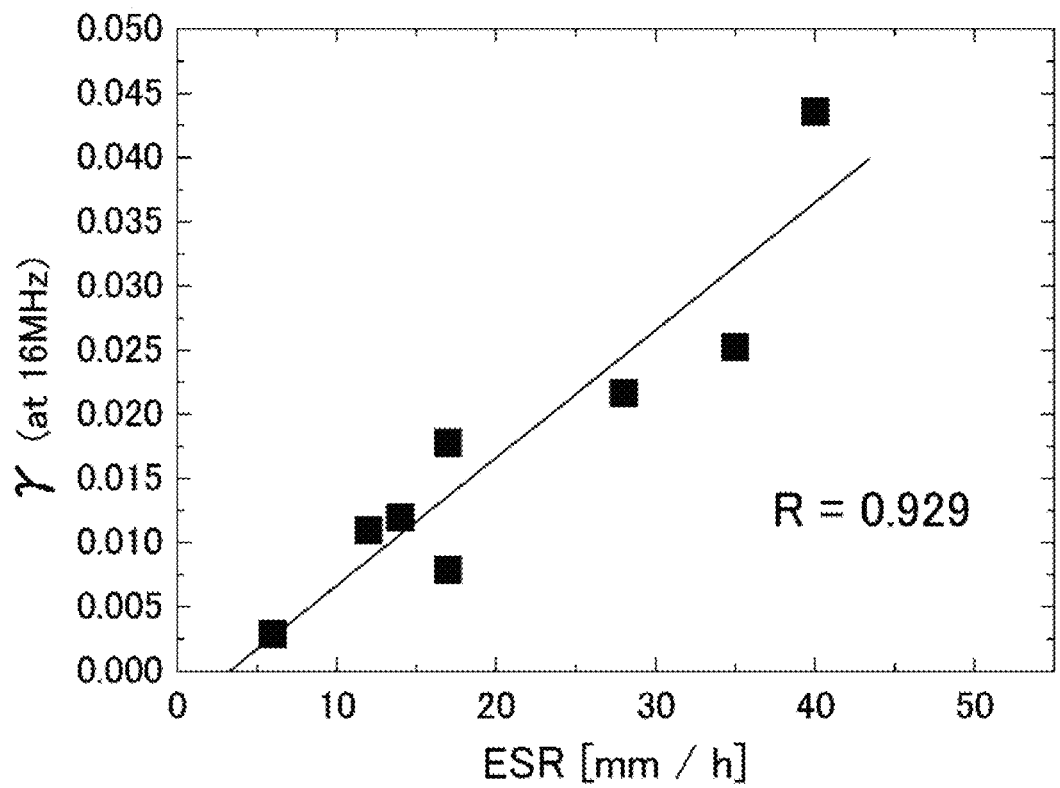

FIG. 15
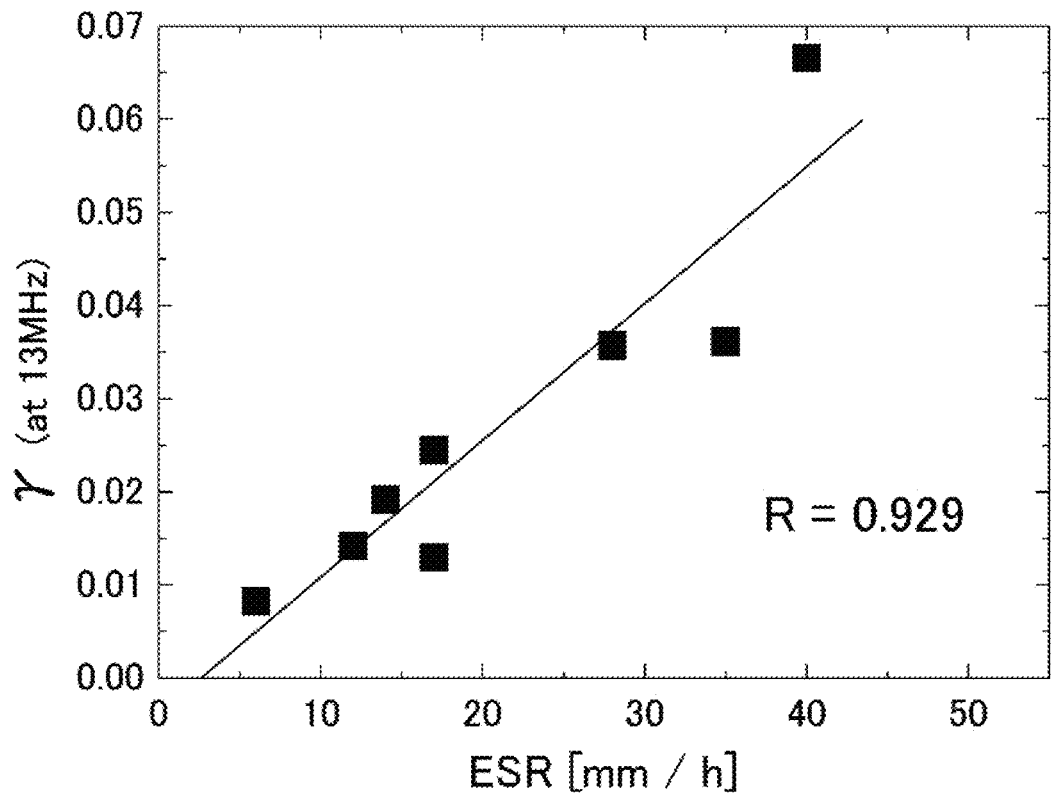
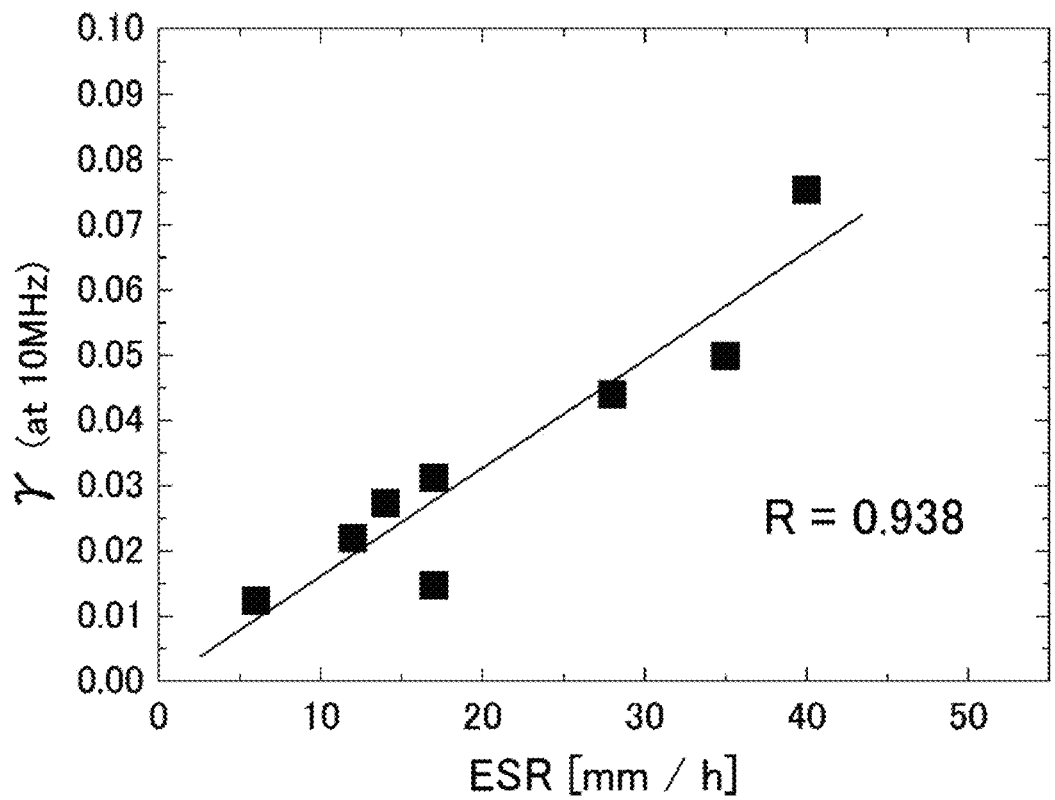

FIG. 16
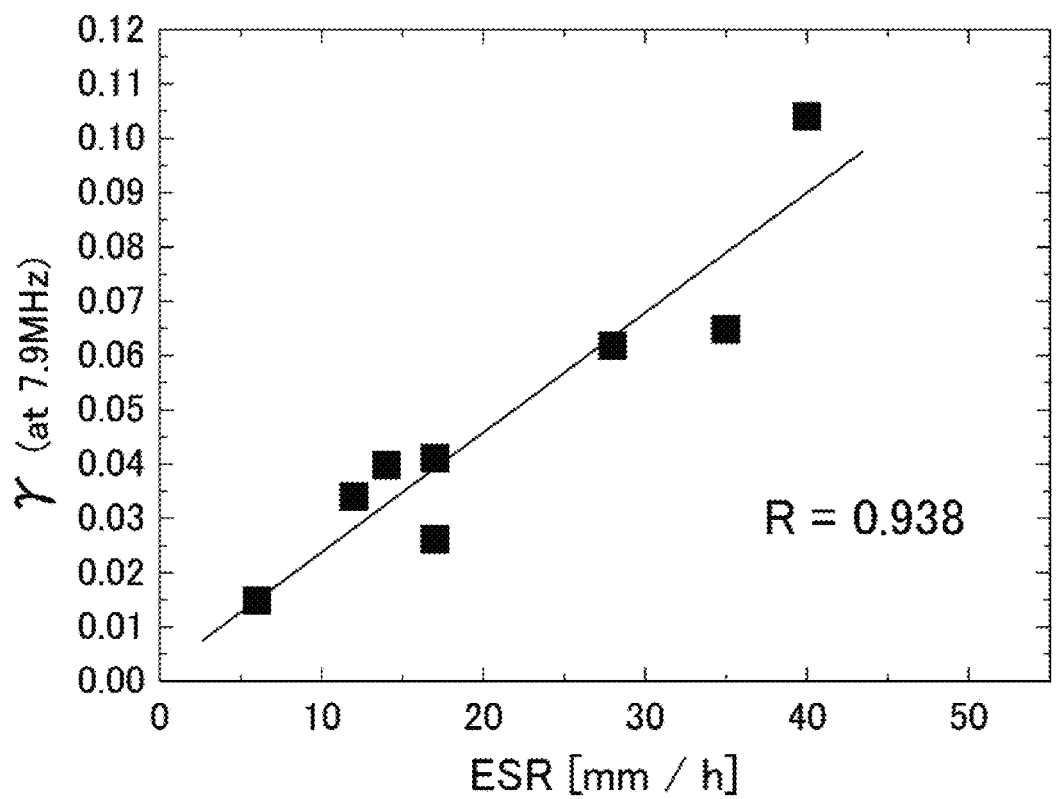
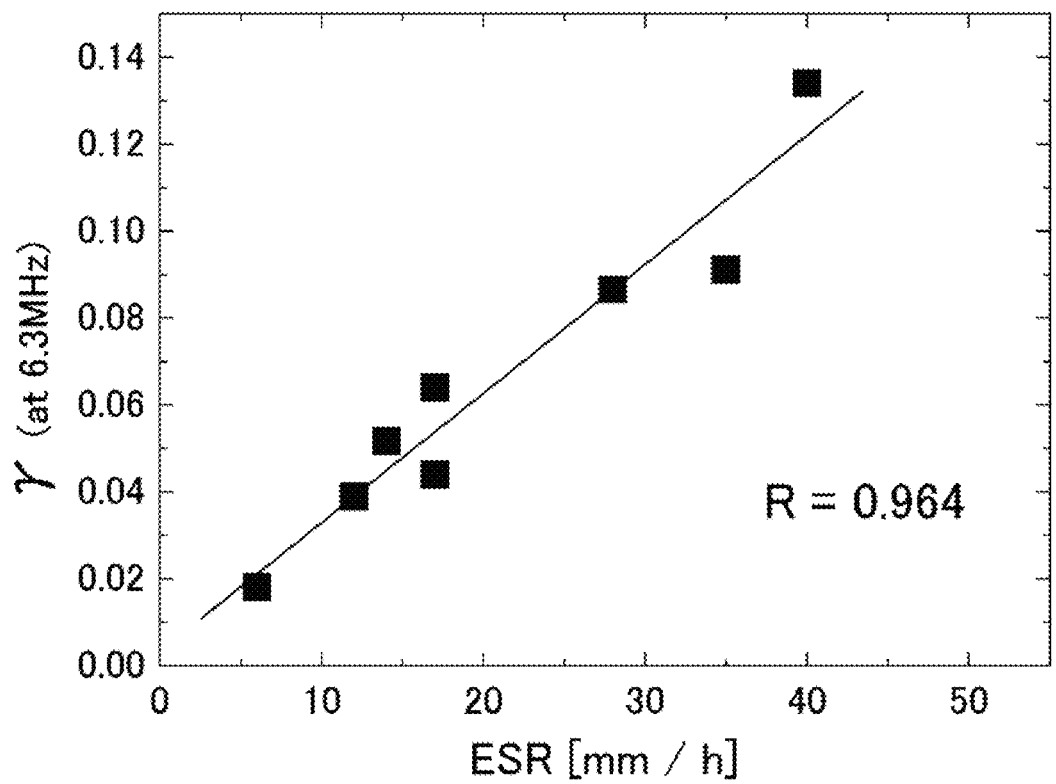

FIG. 17
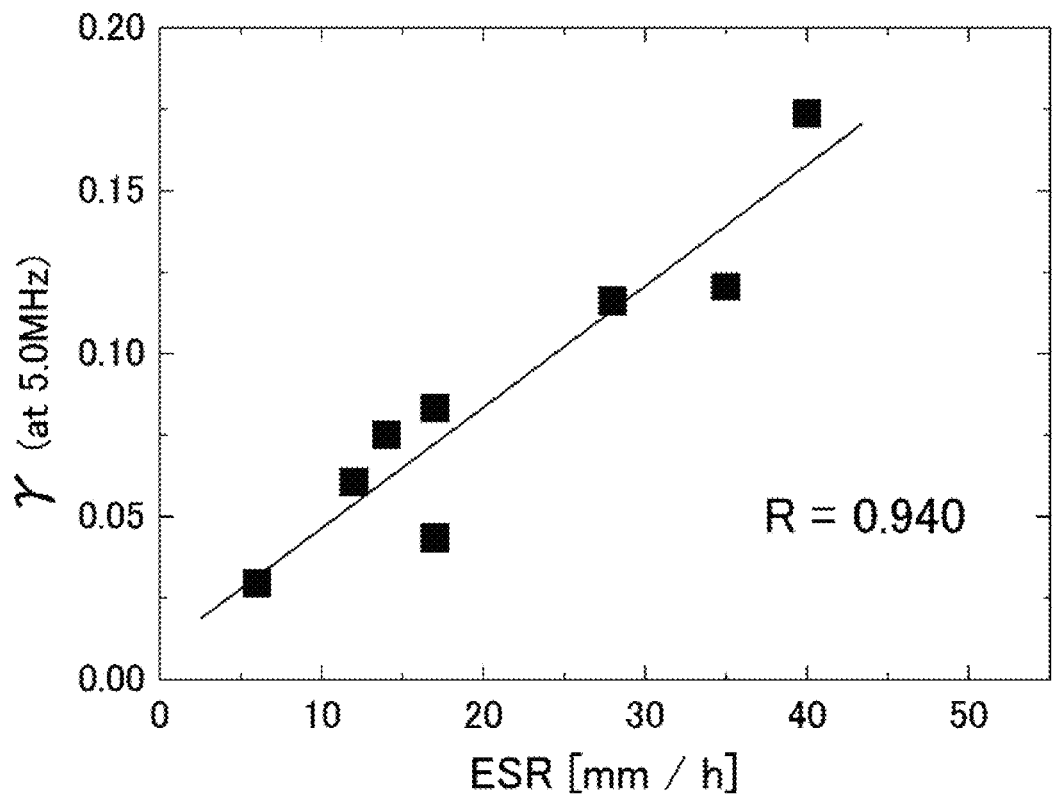
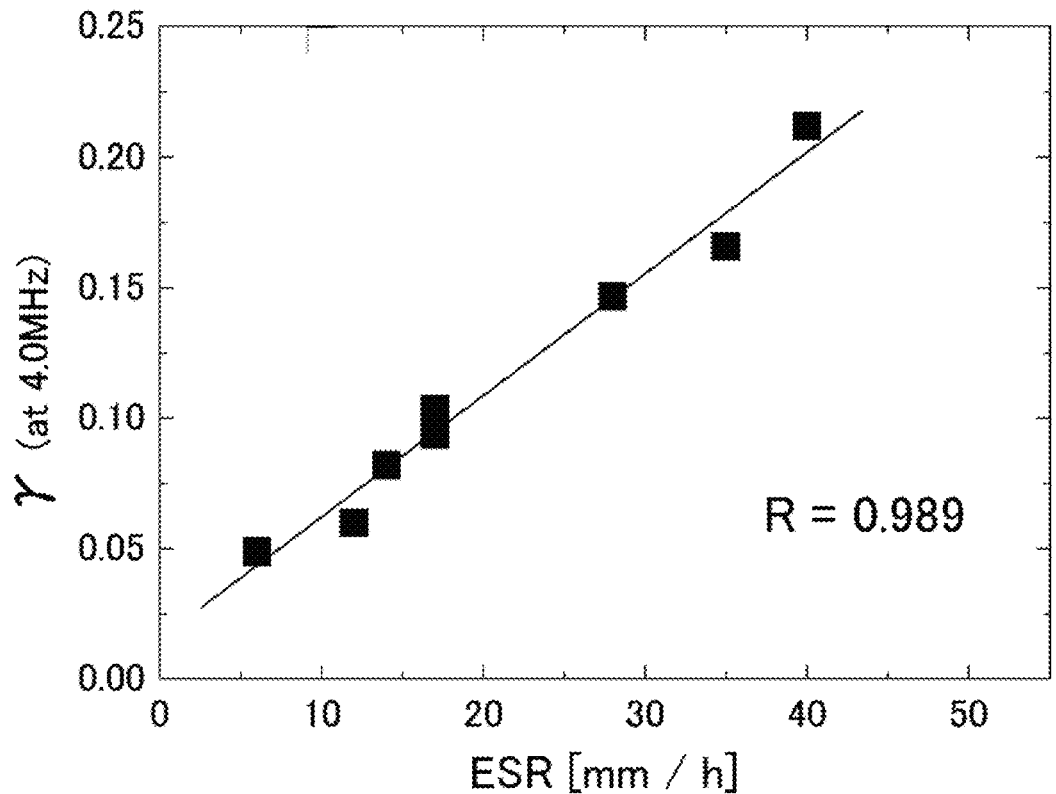

FIG. 18
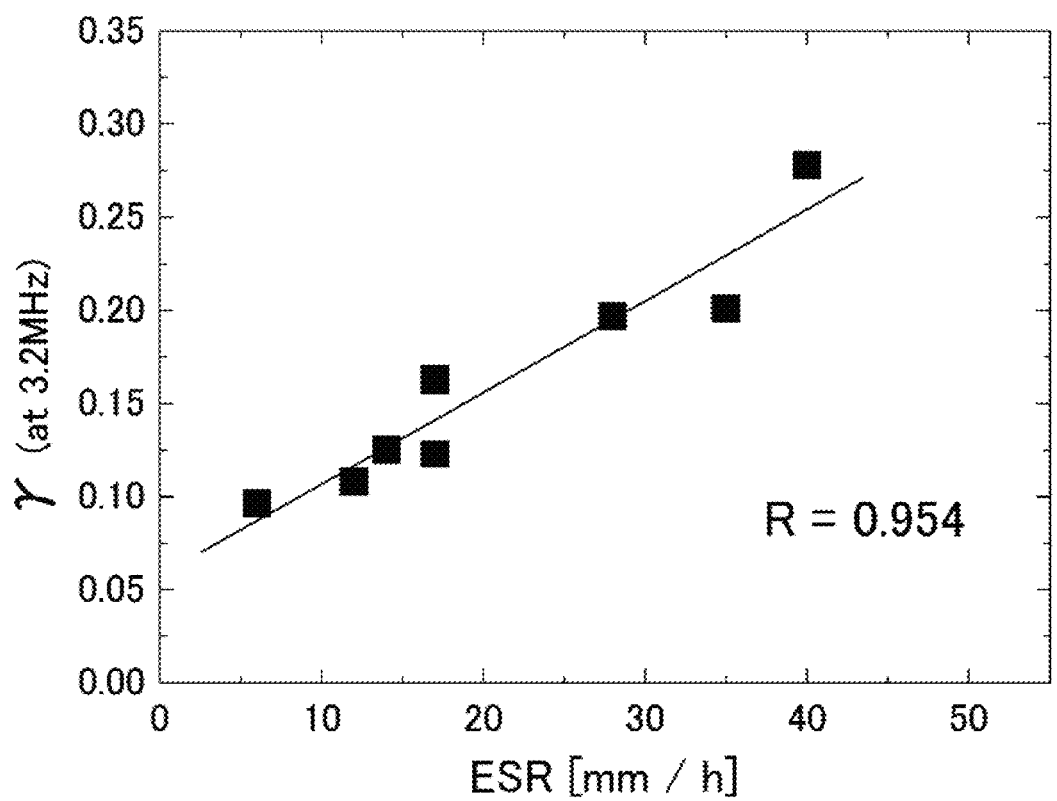
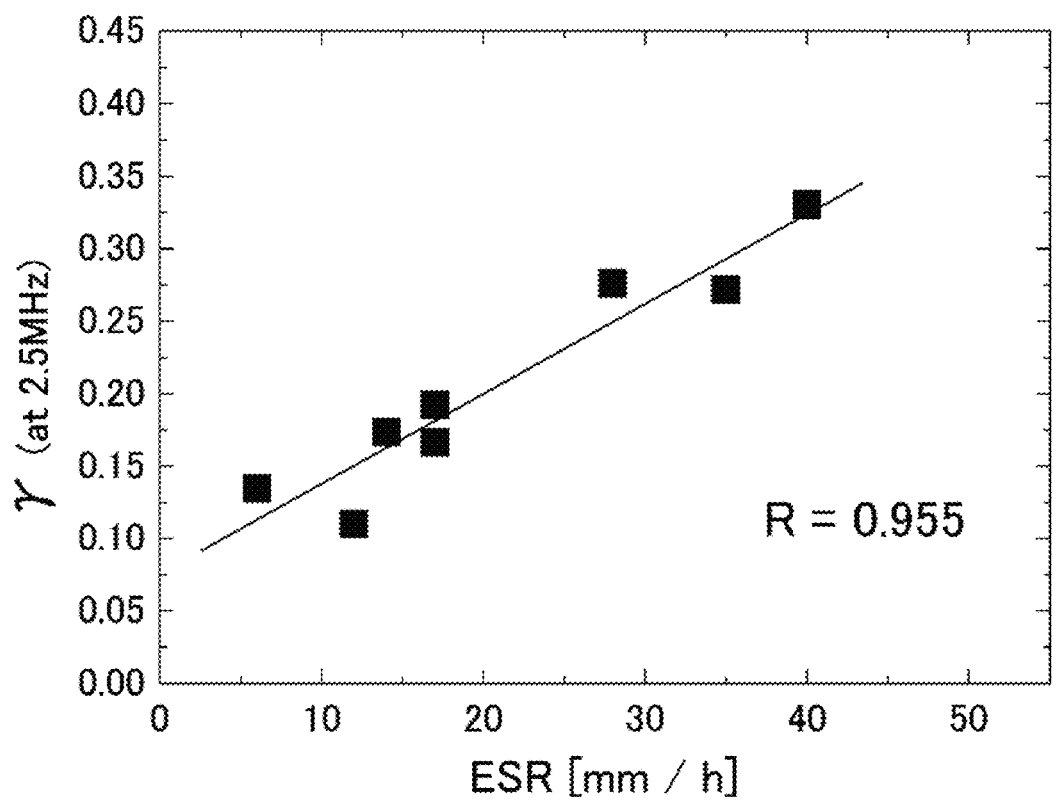

FIG. 20
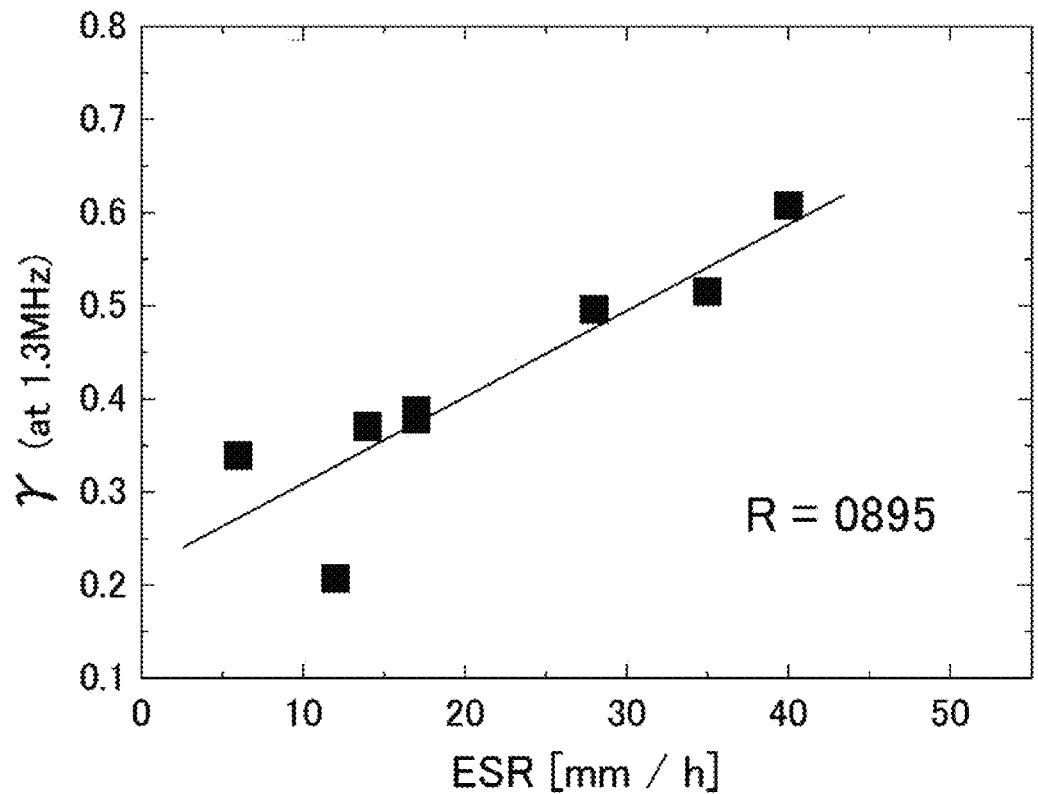
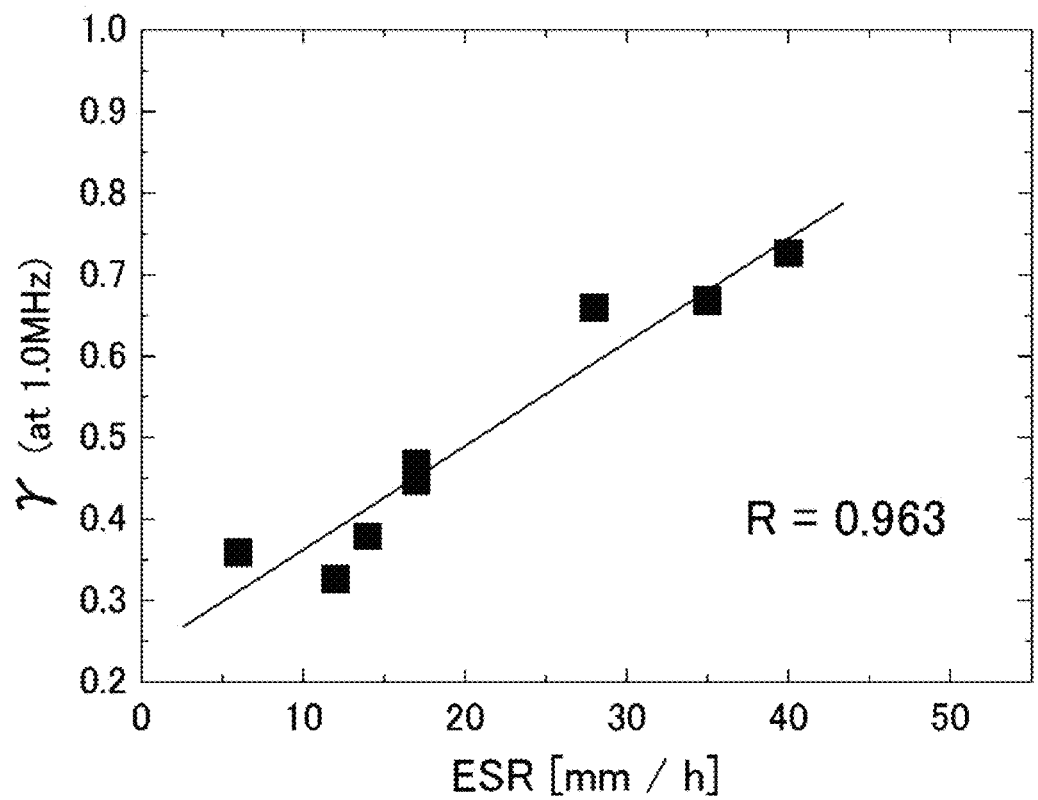

FIG.21
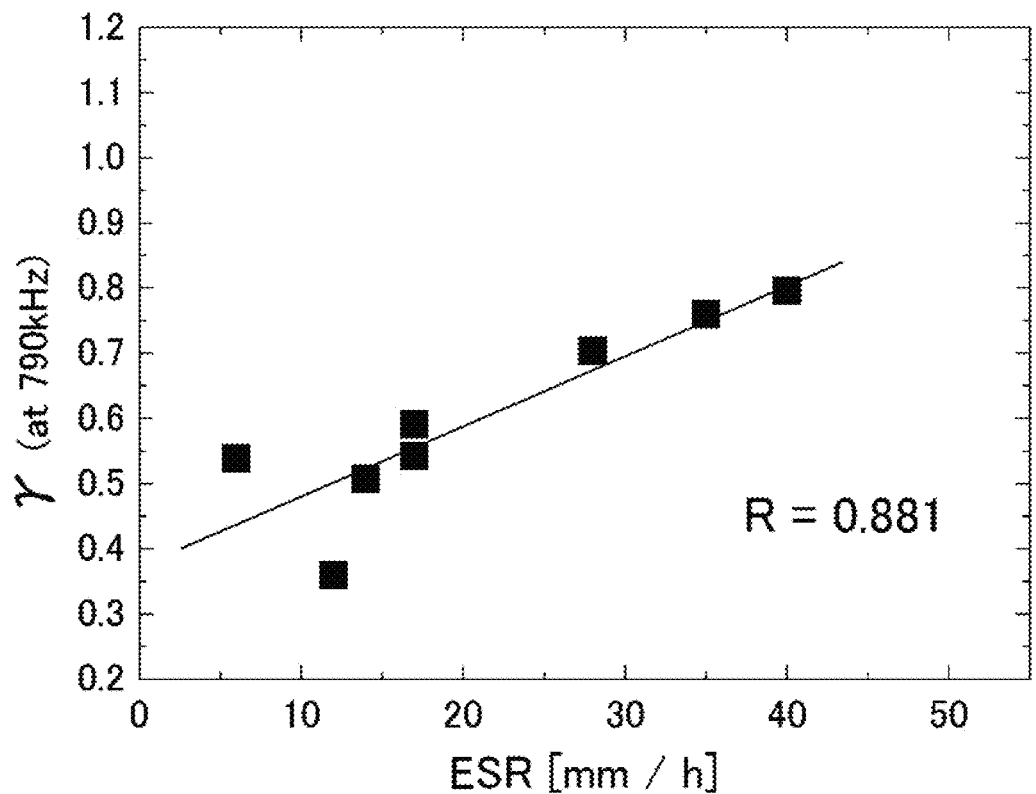
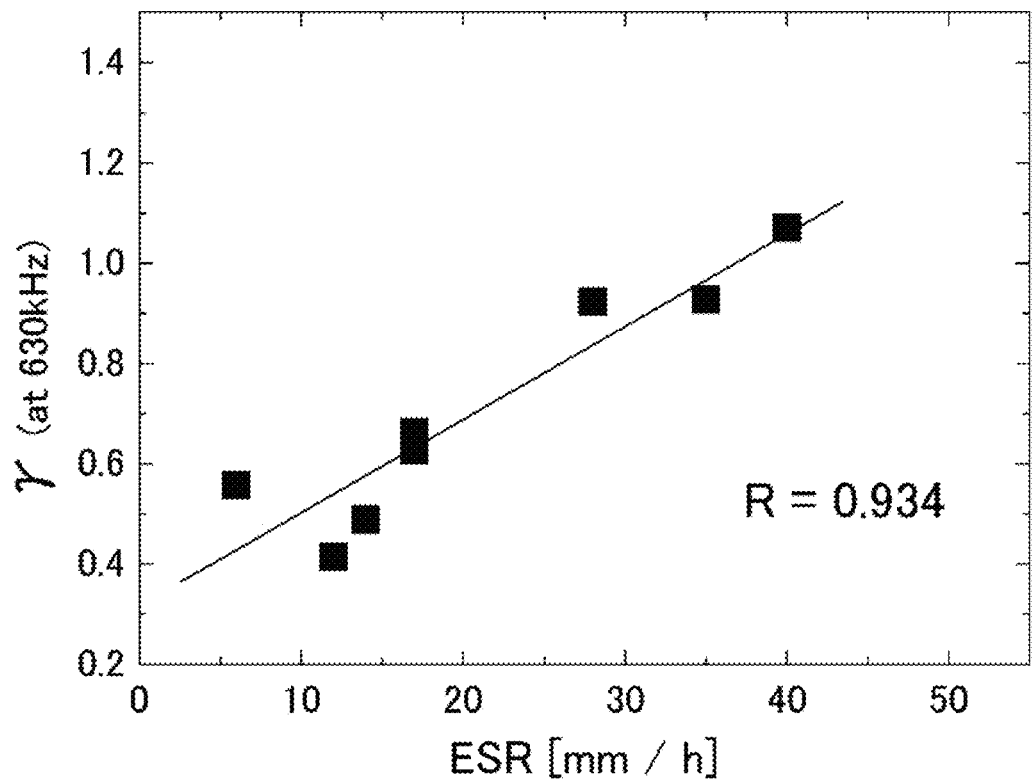

FIG.22
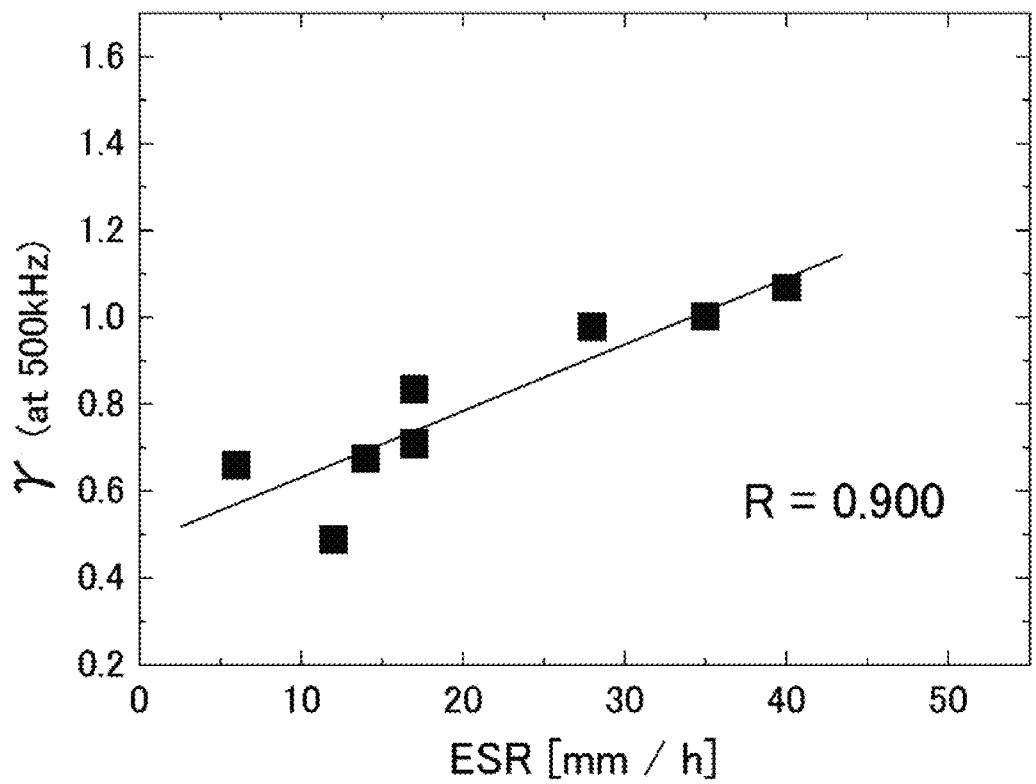
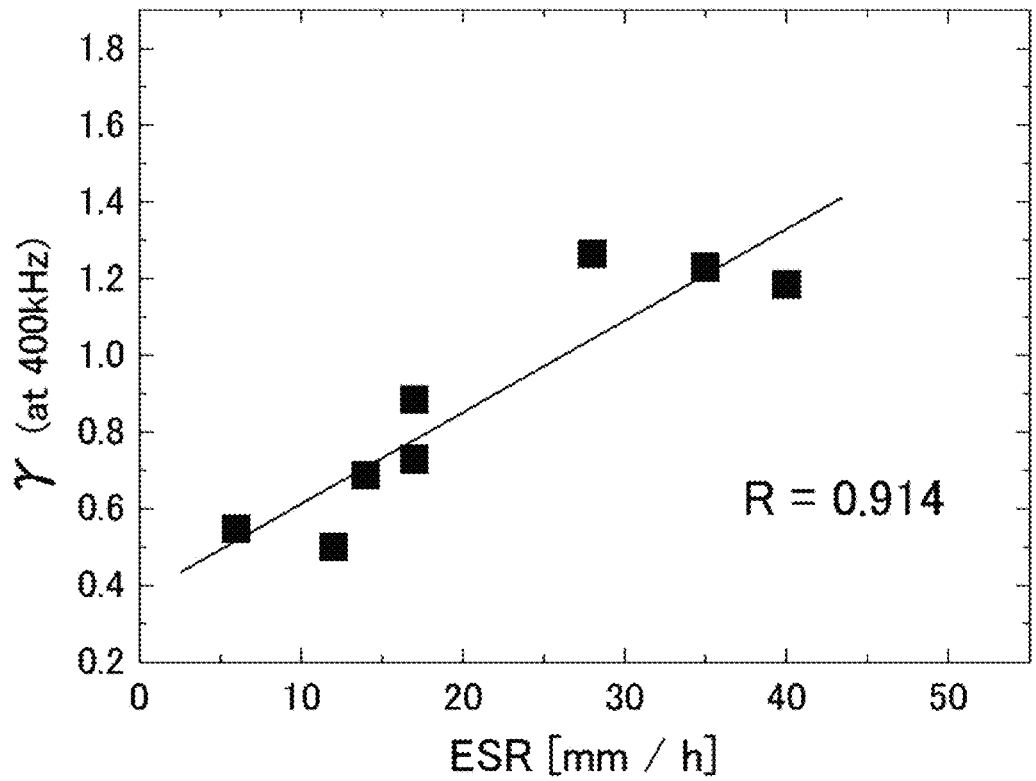

FIG.23
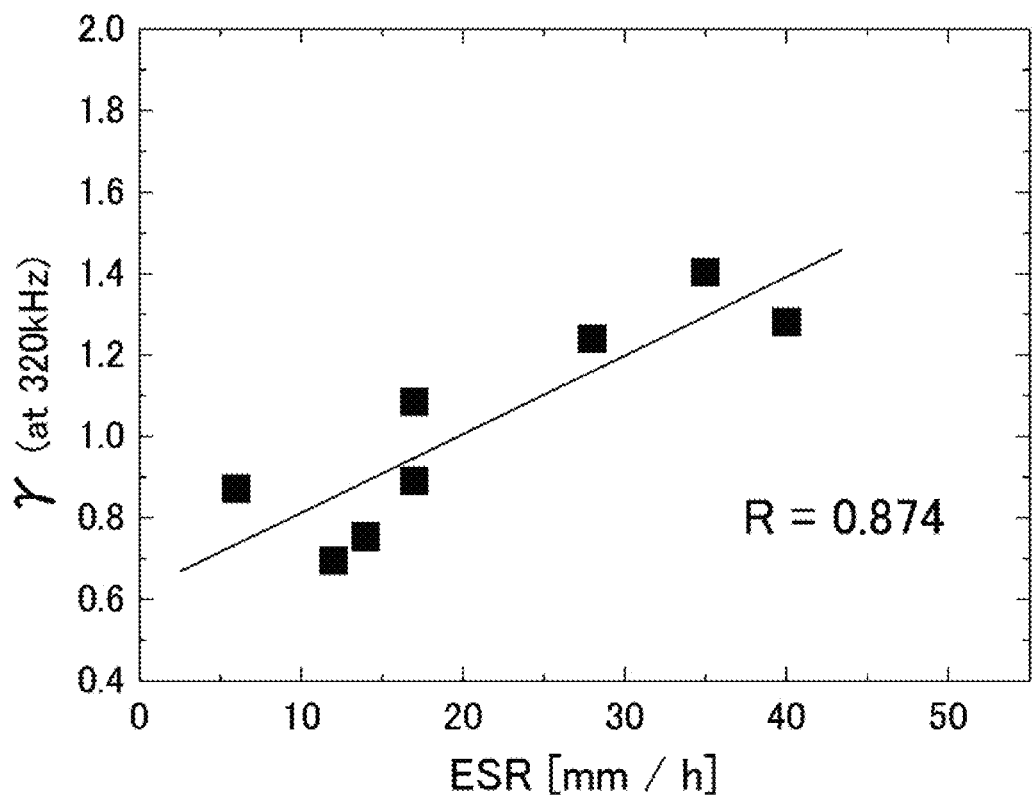
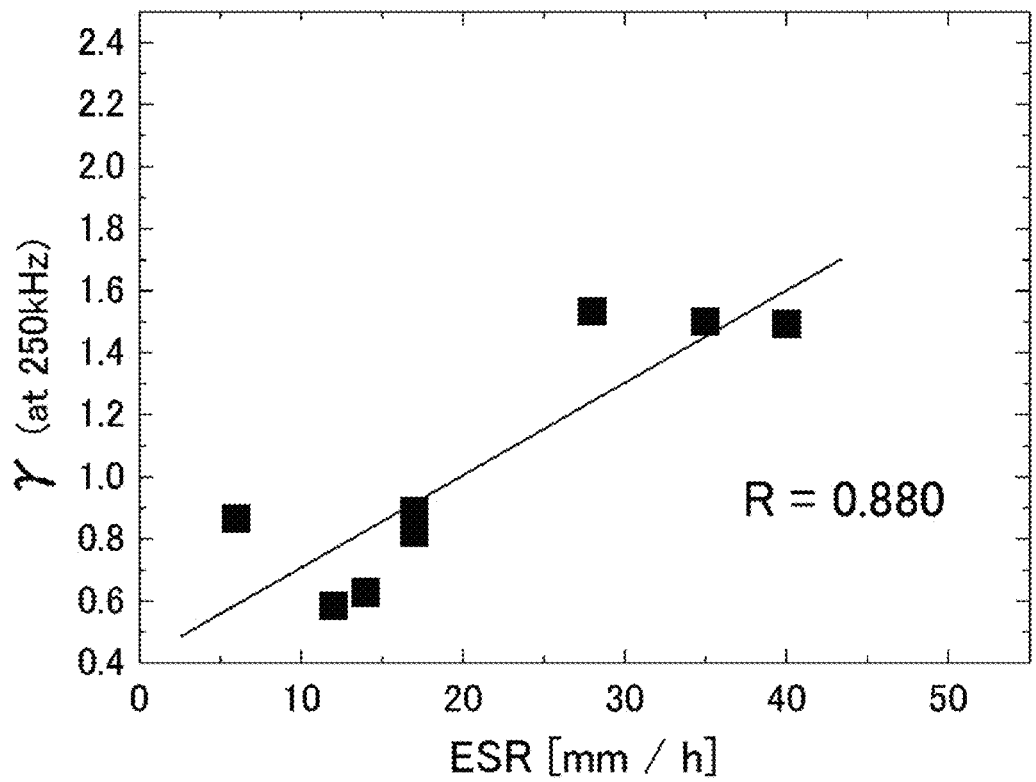

FIG.24
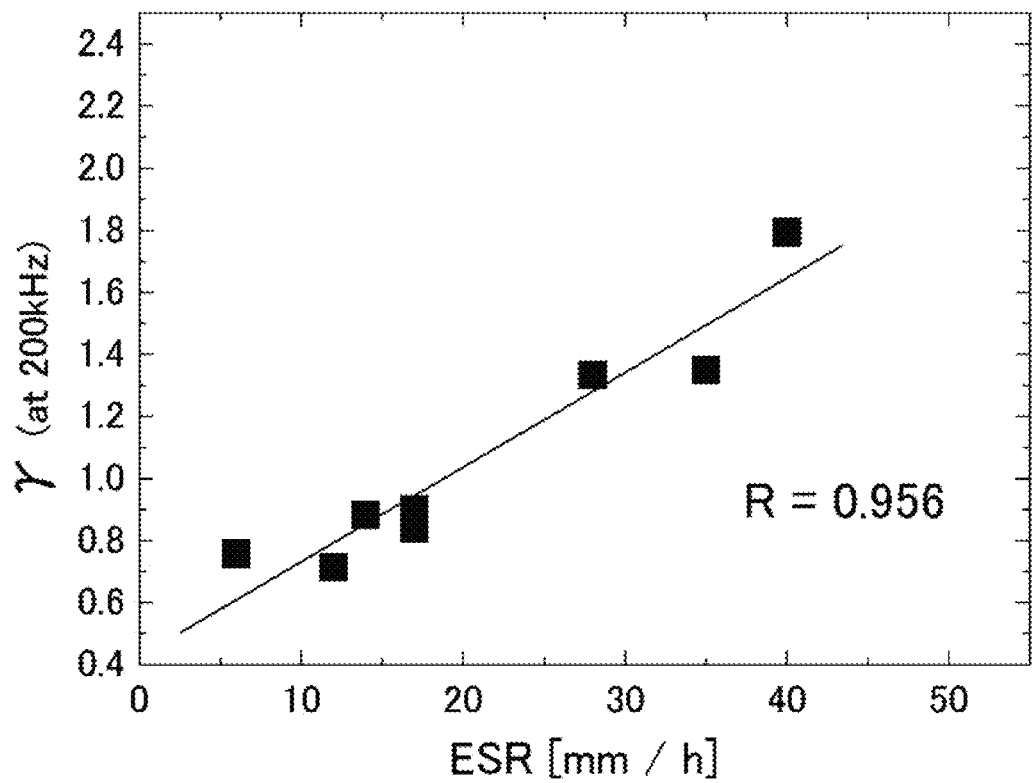
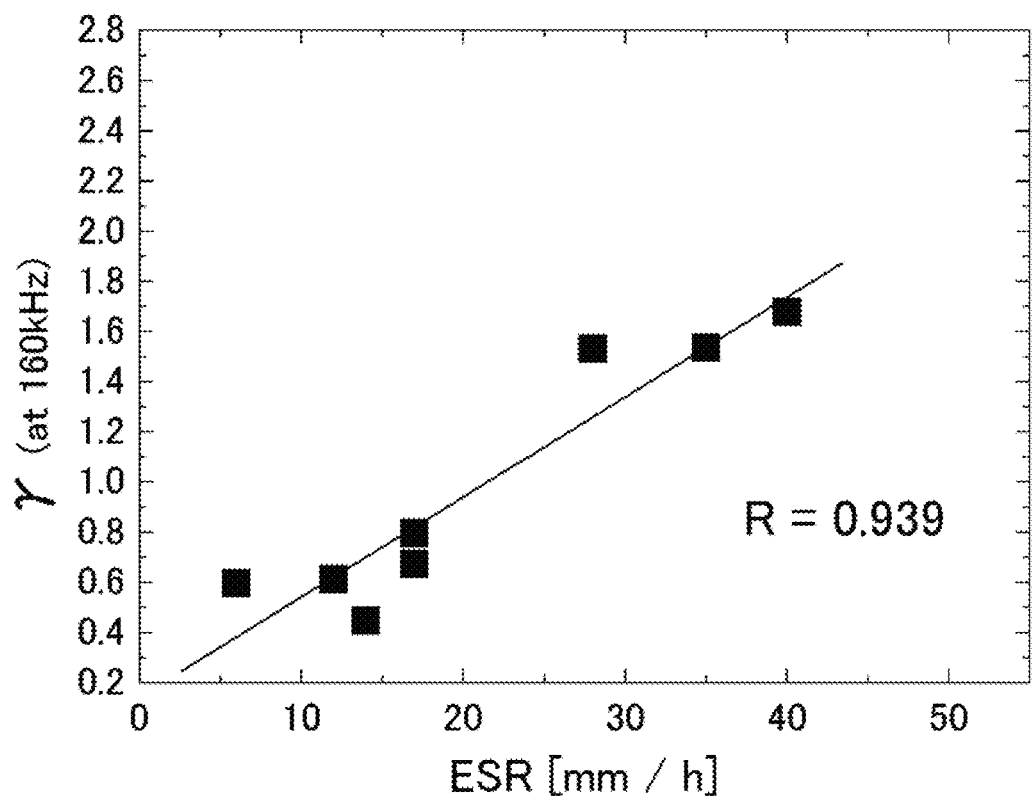

FIG.25
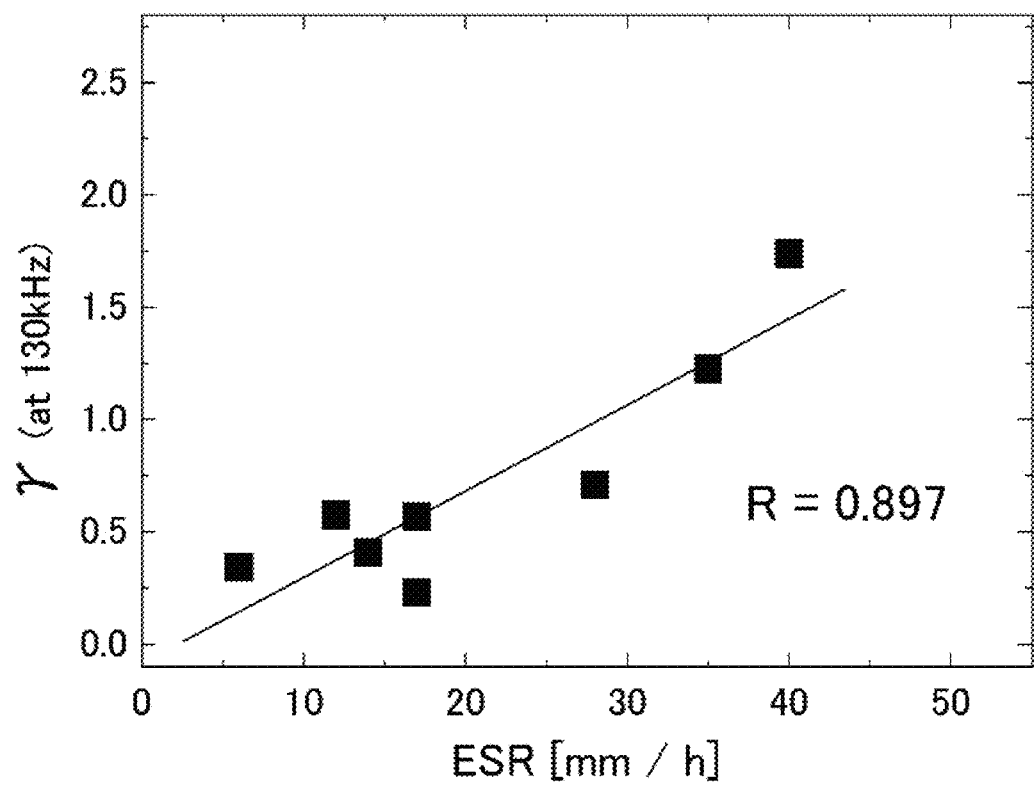
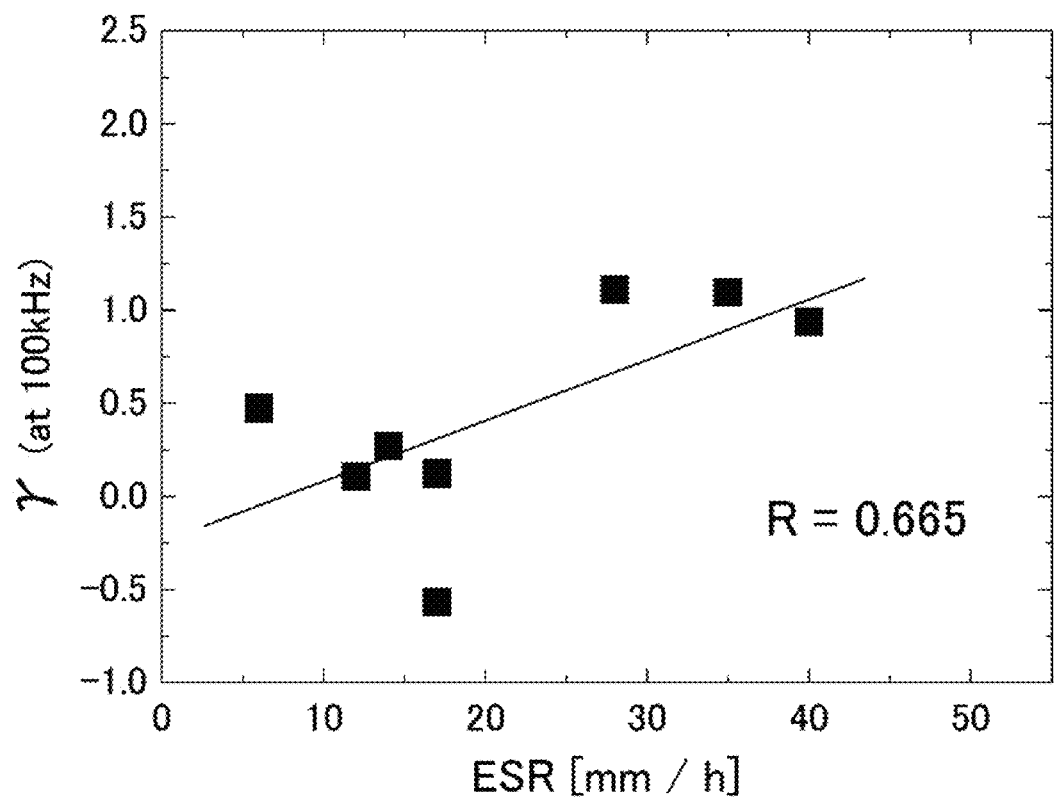

FIG.26
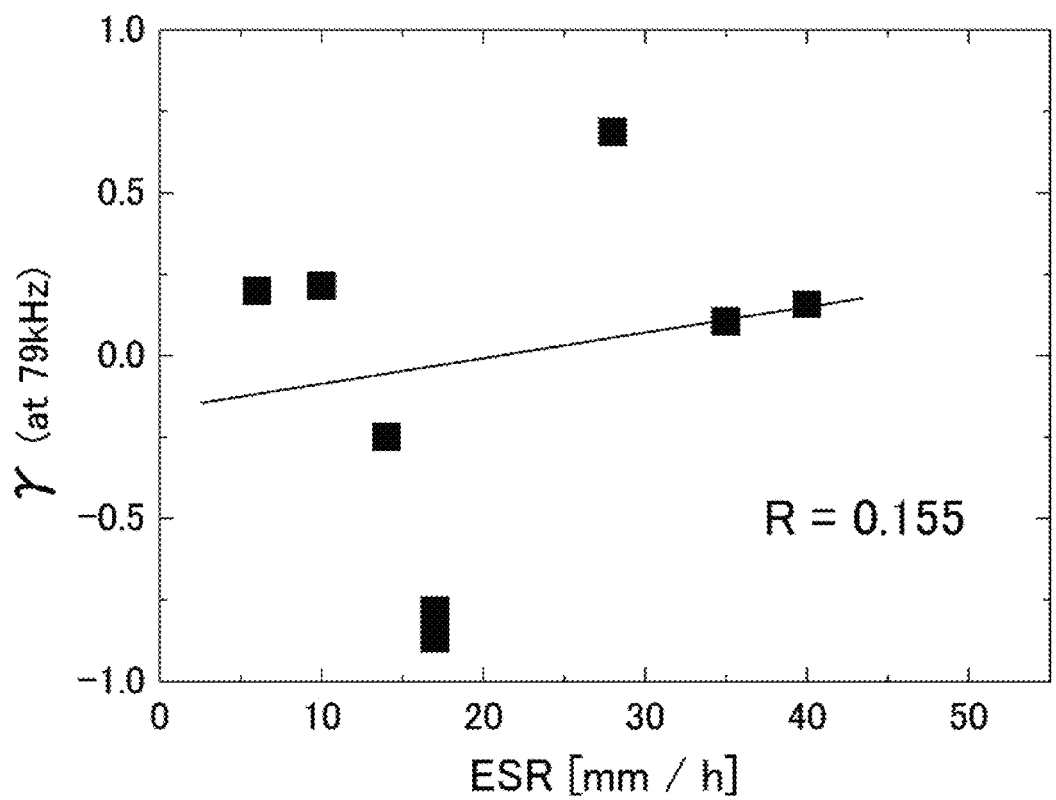
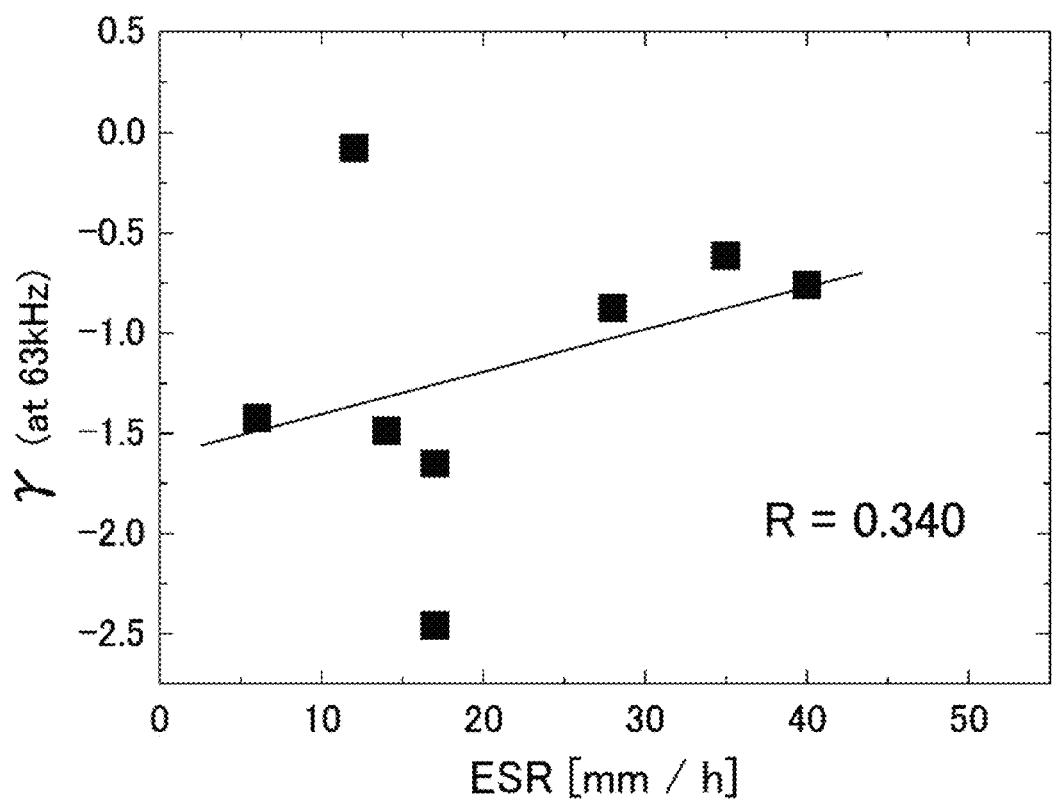

(1)

BLOOD CONDITION ANALYZING DEVICE, BLOOD CONDITION ANALYZING SYSTEM, BLOOD CONDITON ANALYZING METHOD, AND BLOOD CONDITION ANALYZING PROGRAM FOR CAUSING COMPUTER TO EXECUTE THE METHOD

CROSS REFERENCE TO RELATED APPLICATIONS

This application claims the benefit under 35 U.S.C. § 371 as a U.S. National Stage Entry of International Application No. PCT/JP2014/053997, filed in the Japanese Patent Office as a Receiving Office on Feb. 20, 2014, which claims priority to Japanese Patent Application Number 2013-052664, filed in the Japanese Patent Office on Mar. 15, 2013, each of which is hereby incorporated by reference in its entirety.

TECHNICAL FIELD

The present technology relates to a blood condition analyzing device. More specifically, the present technology relates to a blood condition analyzing device, a blood condition analyzing system, and a blood condition analyzing method capable of analyzing the hematocrit value and/or the hemoglobin amount, the rouleaux formation of erythrocytes, etc. of a blood sample from the electrical characteristics of the blood sample, and a program for causing a computer to execute the method.

BACKGROUND ART

As a method for obtaining the volume fraction of cells in a cell suspension, a method using the low frequency electrical conductivity (a frequency of 100 kHz or less) of the suspension and the low frequency electrical conductivity of a solvent containing no cells (a frequency of 100 kHz or less) is known (Non-Patent Literature 1). For example, in a suspension in which spherical cells are dispersed thinly, the volume fraction of cells can be obtained in the manner of Mathematical Formula (1) below.

[Math. 1]

$$\phi = 2\frac{\kappa_a - \kappa_b}{2\kappa_a + \kappa_b} \quad (1)$$

$\phi$: volume fraction
$K_a$: electrical conductivity of solvent
$K_b$: electrical conductivity of suspension On the other hand, in the case where the shape of the cell suspended is not spherical, it is necessary to consider also the shape of the cell; for example, in a suspension in which spheroidal cells are dispersed thinly, the volume fraction of cells can be obtained in the manner of Mathematical Formula (2) below.

[Math. 2]

$$\phi = 9\left(\frac{1}{1-Lz} + \frac{2}{1-L(x=y)}\right)^{-1} \cdot \frac{\kappa_a - \kappa_b}{2\kappa_a + \kappa_b} \quad (2)$$

$\phi$: volume fraction
$K_a$: electrical conductivity of suspension
$K_b$: electrical conductivity of suspension
Lx, Ly, Lz: parameters related to shape etc. of spheroid In a thick suspension that has a high density of cells and cannot be treated as a thin dispersion system, it is necessary to use another formula taking the interaction between cells into consideration.

However, in these conventional methods, it is necessary to use the electrical conductivity of a solvent containing no cells, and the volume fraction of cells cannot be found from data of the suspension alone. Furthermore, the cells need to be dispersed, not aggregated, in the solvent. Hence, for example, in the case of blood containing blood plasma components, the volume fraction etc. of erythrocyte cannot be found by conventional methods because in general rouleaux, aggregation, etc. of erythrocytes will occur. In addition, the degree of rouleaux or aggregation will change variously depending on the flowing of blood and the time from being allowed to stand; thus, it will be difficult to find a calculation formula in which the degree of rouleaux or aggregation is taken into account, and such a mathematical formula is not known at present.

A rouleau (aggregation) of erythrocytes will be formed in a way that an aggregate grows linearly in the beginning and then a spherical structure is formed (Non-Patent Literature 2). Then, the aggregate that has grown to a spherical structure will start to settle down (the sedimentation of erythrocytes (erythrocyte sedimentation)). Here, it is presumed that the larger the size of one erythrocyte aggregate is, the higher the erythrocyte sedimentation rate is. In clinical terms, since erythrocyte sedimentation is exacerbated by infectious diseases etc., it has been used as an important item of a blood test from old times to the present.

These days, a technology of simply and accurately evaluating the degree of coagulation of blood, not rouleaux (aggregation) of erythrocytes, is being developed. For example, Patent Literature 1 discloses a technology in which information on blood coagulation is acquired from the dielectric constant of blood, and describes "a blood coagulation system analyzing device including a pair of electrodes, applying means for applying an AC voltage to the pair of electrodes at prescribed time intervals, measuring means for measuring the dielectric constant of blood disposed between the pair of electrodes, and analyzing means for analyzing the degree of working of a blood coagulation system using the dielectric constant of blood measured at the time intervals after the anticoagulant effect working on the blood is removed."

CITATION LIST

Patent Literature

Patent Literature 1: JP 2010-181400A

Non-Patent Literature

Non-Patent Literature 1: Phys. Med. Biol. 54 (2009) 2395-2405
Non-Patent Literature 2: Blood 70 (1987) 1572-1576

SUMMARY OF INVENTION

Technical Problem

As described above, the development of devices etc. in which the electrical characteristics of a blood sample are measured and the degree of blood coagulation is determined from the measurement results is advanced these days. However, it is the actual situation that a specific application technology in which the technologies mentioned above are applied to a method for obtaining the hematocrit value or to a method for evaluating the rouleaux formation of erythrocytes is not yet realized.

If it is possible to quantitatively evaluate the early process of erythrocyte rouleaux formation, this is expected to correlate with erythrocyte sedimentation and it will be possible to predict the erythrocyte sedimentation rate without waiting for the progress of erythrocyte sedimentation; hence, a speedy test will be possible.

Thus, a main object of the present technology is to provide a technology capable of analyzing the hematocrit value and/or the hemoglobin amount of a blood sample, the rouleaux formation of erythrocytes, etc. on the basis of the electrical characteristics of the blood sample.

Solution to Problem

The present inventors made extensive research on the correlation between the electrical characteristics of blood and the condition of blood. Consequently, the present inventors have found that electrical characteristics at a specific frequency are less susceptible to erythrocyte rouleaux and fluctuate little during the time until the blood coagulation reaction reaches a certain level, and have completed the present technology.

According to the present technology, there is provided a blood condition analyzing device including: an erythrocyte quantitative evaluation unit configured to evaluate a hematocrit value and/or a hemoglobin amount on the basis of an electrical characteristic of a blood sample at a frequency of 2 to 25 MHz.

In addition, there is provided a blood condition analyzing device including: a blood rouleaux evaluation unit configured to evaluate rouleaux formation of erythrocytes by dividing temporal change data of an electrical characteristic of a blood sample at a prescribed frequency by electrical measurement data of the blood sample at a frequency of 2 to 25 MHz.

In the blood condition analyzing device according to the present technology, as the temporal change data of the electrical characteristic, a difference between an electrical characteristic of the blood sample at a time when rouleaux have proceeded and an electrical characteristic of the blood sample before rouleaux proceed may be used.

In the blood condition analyzing device according to the present technology, as the temporal change data of the electrical characteristic, temporal change data of the electrical characteristic of the blood sample at a frequency of 100 kHz to 40 MHz may be used.

The blood condition analyzing device according to the present technology may further includes an erythrocyte sedimentation evaluation unit configured to evaluate a degree of erythrocyte sedimentation on the basis of rouleaux formation evaluation evaluated by the blood rouleaux evaluation unit.

The blood condition analyzing device according to the present technology may further includes a blood coagulation evaluation unit configured to evaluate a degree of blood coagulation on the basis of an electrical characteristic of a blood sample.

The blood condition analyzing device according to the present technology may further includes a measuring unit configured to measure an electrical characteristic of a blood sample over time.

Next, according to the present technology, there is provided a blood condition analyzing system including: an electrical characteristic measuring device including a measuring unit configured to measure an electrical characteristic of blood over time; and a blood condition analyzing device including an erythrocyte quantitative evaluation unit configured to evaluate a hematocrit value and/or a hemoglobin amount on the basis of an electrical characteristic of a blood sample at a frequency of 2 to 25 MHz.

In addition, there is provided a blood condition analyzing system including: an electrical characteristic measuring device including a measuring unit configured to measure an electrical characteristic of blood over time; and a blood condition analyzing device including a blood rouleaux evaluation unit configured to evaluate rouleaux formation of erythrocytes by dividing temporal change data of an electrical characteristic of a blood sample at a prescribed frequency by electrical measurement data of the blood sample at a frequency of 2 to 25 MHz.

In the blood condition analyzing system according to the present technology may further includes a server including an information storage unit configured to store a measurement result in the electrical characteristic measuring device and/or an analysis result in the blood condition analyzing device.

In this case, the server may be connected to the electrical characteristic measuring device and/or the blood condition analyzing device via a network.

In addition, according to the present technology, there is provided a blood condition analyzing method including an erythrocyte quantitative evaluation process of evaluating a hematocrit value and/or a hemoglobin amount on the basis of an electrical characteristic of a blood sample at a frequency of 2 to 25 MHz.

In addition, there is provided a blood condition analyzing method including a blood rouleaux evaluation process of evaluating rouleaux formation of erythrocytes by dividing temporal change data of an electrical characteristic of a blood sample at a prescribed frequency by electrical measurement data of the blood sample at a frequency of 2 to 25 MHz.

In addition, according to the present technology, there is provided a blood condition analyzing program for causing a computer to execute an erythrocyte quantitative evaluation function of evaluating a hematocrit value and/or a hemoglobin amount on the basis of an electrical characteristic of a blood sample at a frequency of 2 to 25 MHz.

In addition, there is provided a blood condition analyzing program for causing a computer to execute a blood rouleaux evaluation function of evaluating rouleaux formation of erythrocytes by dividing temporal change data of an electrical characteristic of a blood sample at a prescribed frequency by electrical measurement data of the blood sample at a frequency of 2 to 25 MHz.

Advantageous Effects of Invention

According to the present technology, it becomes possible to analyze the hematocrit value and/or the hemoglobin amount of a blood sample, the rouleaux formation of erythrocytes, etc. on the basis of the electrical characteristics of the blood sample; consequently, it becomes possible to predict the erythrocyte sedimentation rate, and a speedy test can be provided.

BRIEF DESCRIPTION OF DRAWINGS

FIG. 4 is drawing-substitute graphs showing the relationship between the dielectric constant and the hematocrit value at each frequency found in Example 1.

FIG. 5 is drawing-substitute graphs showing the relationship between the dielectric constant and the hematocrit value at each frequency found in Example 1.

FIG. 6 is drawing-substitute graphs showing the relationship between the dielectric constant and the hematocrit value at each frequency found in Example 1.

FIG. 7 is drawing-substitute graphs showing the relationship between the dielectric constant and the hematocrit value at each frequency found in Example 1.

FIG. 8 is drawing-substitute graphs showing the relationship between the dielectric constant and the hematocrit value at each frequency found in Example 1.

FIG. 9 is drawing-substitute graphs showing the relationship between the dielectric constant and the hematocrit value at each frequency found in Example 1.

FIG. 11 is drawing-substitute graphs showing the relationship between the dielectric constant and the hematocrit value at each frequency found in Example 1.

FIG. 13 is drawing-substitute graphs showing the relationship between the blood rouleaux evaluation value ($\gamma$) and the erythrocyte sedimentation rate (ESR) at each frequency found in Example 2.

FIG. 14 is drawing-substitute graphs showing the relationship between the blood rouleaux evaluation value ($\gamma$) and the erythrocyte sedimentation rate (ESR) at each frequency found in Example 2.

FIG. 15 is drawing-substitute graphs showing the relationship between the blood rouleaux evaluation value ($\gamma$) and the erythrocyte sedimentation rate (ESR) at each frequency found in Example 2.

FIG. 16 is drawing-substitute graphs showing the relationship between the blood rouleaux evaluation value ($\gamma$) and the erythrocyte sedimentation rate (ESR) at each frequency found in Example 2.

FIG. 17 is drawing-substitute graphs showing the relationship between the blood rouleaux evaluation value ($\gamma$) and the erythrocyte sedimentation rate (ESR) at each frequency found in Example 2.

FIG. 18 is drawing-substitute graphs showing the relationship between the blood rouleaux evaluation value ($\gamma$) and the erythrocyte sedimentation rate (ESR) at each frequency found in Example 2.

FIG. 20 is drawing-substitute graphs showing the relationship between the blood rouleaux evaluation value ($\gamma$) and the erythrocyte sedimentation rate (ESR) at each frequency found in Example 2.

FIG. 21 is drawing-substitute graphs showing the relationship between the blood rouleaux evaluation value ($\gamma$) and the erythrocyte sedimentation rate (ESR) at each frequency found in Example 2.

FIG. 22 is drawing-substitute graphs showing the relationship between the blood rouleaux evaluation value ($\gamma$) and the erythrocyte sedimentation rate (ESR) at each frequency found in Example 2.

FIG. 23 is drawing-substitute graphs showing the relationship between the blood rouleaux evaluation value ($\gamma$) and the erythrocyte sedimentation rate (ESR) at each frequency found in Example 2.

FIG. 24 is drawing-substitute graphs showing the relationship between the blood rouleaux evaluation value ($\gamma$) and the erythrocyte sedimentation rate (ESR) at each frequency found in Example 2.

FIG. 25 is drawing-substitute graphs showing the relationship between the blood rouleaux evaluation value ($\gamma$) and the erythrocyte sedimentation rate (ESR) at each frequency found in Example 2.

FIG. 26 is drawing-substitute graphs showing the relationship between the blood rouleaux evaluation value ($\gamma$) and the erythrocyte sedimentation rate (ESR) at each frequency found in Example 2.

DESCRIPTION OF EMBODIMENTS

Figure 1:
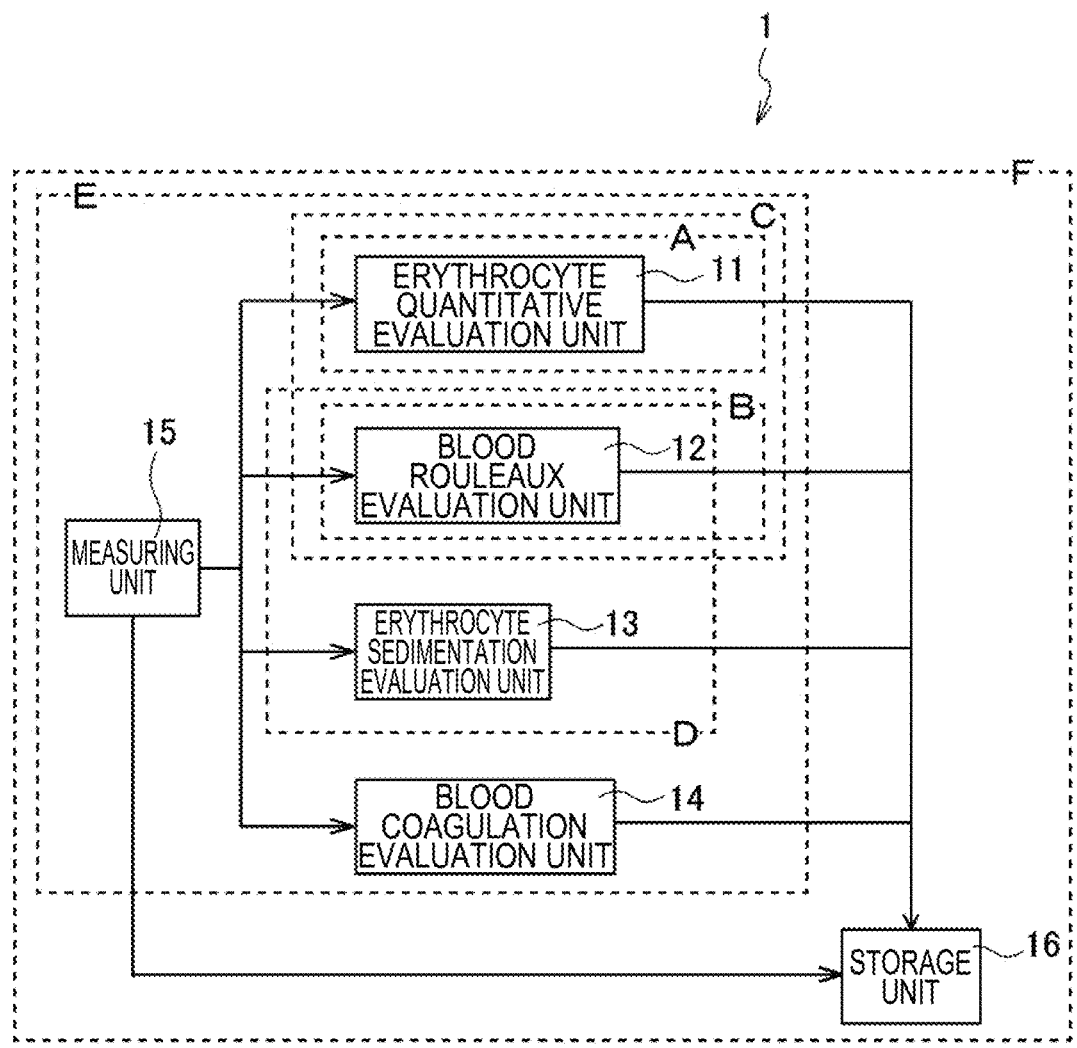
FIG. 1 is a schematic conceptual diagram schematically showing the concept of a blood condition analyzing device 1 according to the present technology.

Hereinbelow, preferred embodiments for carrying out the present technology are described with reference to the drawings. The embodiments described below are examples of the typical embodiments of the present technology, and the scope of the present technology is not construed as being limited by the embodiments. The description is given in the following order:

1. Blood condition analyzing device 1
(1) Erythrocyte quantitative evaluation unit 11
(2) Blood rouleaux evaluation unit 12
(3) Erythrocyte sedimentation evaluation unit 13
(4) Blood coagulation evaluation unit 14
(5) Measuring unit 15
(6) Storage unit 16
(7) Blood sample
2. Blood condition analyzing system 10
(1) Electrical characteristic measuring device 101
(2) Blood condition analyzing device 1
(3) Server 102
(4) Display unit 103
(5) User interface 104
3. Blood condition analyzing method
(1) Erythrocyte quantitative evaluation process I
(2) Blood rouleaux evaluation process II (3) Erythrocyte sedimentation evaluation process III
(4) Blood coagulation evaluation process IV
(5) Measuring process V 4. Blood condition analyzing program 1. Blood Condition Analyzing Device 1

FIG. 1 is a schematic conceptual diagram schematically showing the concept of a blood condition analyzing device 1 according to the present technology. The blood condition analyzing device 1 according to the present technology includes at least an erythrocyte quantitative evaluation unit 11 or a blood rouleaux evaluation unit 12. The blood condition analyzing device 1 may include, as necessary, an erythrocyte sedimentation evaluation unit 13, a blood coagulation evaluation unit 14, a measuring unit 15, a storage unit 16, etc. Each component will now be described in detail.

(1) Erythrocyte Quantitative Evaluation Unit 11

The reference character A in FIG. 1 is a schematic conceptual diagram schematically showing the concept of a first embodiment of the blood condition analyzing device 1 according to the present technology. In the erythrocyte quantitative evaluation unit 11, the hematocrit value and/or the hemoglobin amount is evaluated on the basis of the electrical characteristics of a blood sample at a specific frequency. The present inventors have found that the electrical characteristics of a blood sample at frequencies of 2 to 25 MHz are less susceptible to erythrocyte rouleaux and fluctuate little in the time until the blood coagulation reaction reaches a certain level. The present inventors have also found that the electrical characteristics of a blood sample at frequencies of 2 to 25 MHz correlate with the hematocrit value and the hemoglobin amount obtained by a common conventional blood test (see Example 1), and have established a technology that evaluates the hematocrit value and/or the hemoglobin amount from the electrical characteristics of a blood sample at a frequency of 2 to 25 MHz.

For the electrical characteristics of the blood sample, when an external electrical characteristic measuring device is provided or the blood condition analyzing device 1 according to the present technology is provided with the measuring unit 15 described later, the raw data measured in the measuring unit 15 can be used as they are. Alternatively, it is possible to use data in which noise is removed from raw data.

As the electrical characteristics of blood that can be used in the blood condition analyzing device 1 according to the present technology, for example, dielectric constant, impedance, admittance, capacitance, conductance, electrical conductivity, phase angle, etc. may be given. These electrical characteristics can be transformed to each other by the mathematical formulae shown in Table 1 below. Therefore, for example, the evaluation results of the hematocrit value and/or the hemoglobin amount when evaluated using the results of the dielectric constant measurement of a blood sample are the same as the evaluation results when evaluated using the results of the impedance measurement of the same blood sample. Most of these electrical quantities and property values can be described using complex numbers, and the transformation formula can thereby be simplified.

TABLE 1

Principal electrical quantities and property values mutually transformable

| Electrical quantity and property value | Symbol | When expressed using complex number |
|---|---|---|
| Voltage | V | $V^* = \lvert V \rvert \exp j(\omega t + \phi)$ |
| Current | I | $I^* = \lvert I \rvert \exp j(\omega t + \varphi)$ |
| Impedance | Z | $Z^* = R + jX$ (R: resistance, X: reactance) |
| Admittance | Y | $Y^* = G + jB$ (G: conductance, B: susceptance) |
| Capacitance | C | $C^* = C - jG/\omega$ |
| Conductance | G | $G^* = G + j\omega C$ |
| Loss tangent (dielectric, loss tangent) | D or tanδ | |
| Loss angle | δ | |
| Phase angle | θ | |
| Q factor | Q | |
| Dielectric constant | ε | $\varepsilon^* = \varepsilon - j\kappa/\omega\varepsilon_0$ |
| Electrical conductivity | κ | $\kappa^* = \kappa + j\omega\varepsilon_0\varepsilon$ |

Mathematical formula relating each electrical quantity and property value $Z^* = V^*/I^*$
$\theta = \phi - \varphi$
$Y^* = 1/Z^*$
$C = B/\omega$
$D = \tan\delta = G/\omega C = 1/Q$
$\varepsilon^* = C^*/C_0$
$\kappa^* = j\omega\varepsilon_0\varepsilon^*$ ω: angular frequency
$\varepsilon_0$: dielectric constant of vacuum (constant)
$C_0$: constant depending on measuring device etc.
Value marked with *: complex number Specific frequencies for the electrical characteristics of blood which can be used in the blood condition analyzing device 1 according to the present technology are not particularly limited to the extent that they are in the range of 2 to 25 MHz, but are preferably 2 to 10 MHz. The influence of blood rouleaux can be suppressed to a minimum by using electrical characteristics at 2 MHz or more. At frequencies higher than 10 MHz, the electrical response of blood will be weak and the influence of noise will be relatively strong; thus, accurate evaluation can be performed by using electrical characteristics at 10 MHz or less.

As the electrical characteristics of blood used in the blood condition analyzing device 1 according to the first embodiment, electrical characteristics in as early a stage as possible after the start of measurement are preferably used. Specifically, it is preferable to use electrical characteristics within 3 minutes after anticoagulation by an anticoagulant is removed. This is because within 3 minutes after the removal of anticoagulation, the influence by rouleaux or coagulation of blood can be suppressed to a minimum.

(2) Blood Rouleaux Evaluation Unit 12

The reference character B in FIG. 1 is a schematic conceptual diagram schematically showing the concept of a second embodiment of the blood condition analyzing device 1 according to the present technology. In the blood rouleaux evaluation unit 12, the temporal change data of the electrical characteristics of a blood sample at a prescribed frequency is divided by the electrical measurement data of the blood sample at a frequency of 2 to 25 MHz; thereby, the rouleaux formation of erythrocytes is evaluated.

More specifically, as shown in Mathematical Formula (3) below, the difference between the electrical characteristic ($E_2$) of the blood sample at a time ($t_2$) when rouleaux have proceeded and the electrical characteristic ($E_{r1}$) of the blood sample before rouleaux proceed ($t_1$) is divided by the electrical measurement data of the blood sample at a frequency of 2 to 25 MHz, that is, electrical measurement data ($E_{r0}$) correlating with the hematocrit value and/or the hemoglobin amount; thereby, the rouleaux formation of erythrocytes is evaluated.

[Math. 3]

$$\gamma(\text{rouleaux evaluation value}) = \frac{E_{t2}^{f[Hz]} - E_{t1}^{f[Hz]}}{E_{t0}^{2 \sim 25[Hz]}} \quad (3)$$

The electrical characteristics of the blood sample vary with the rouleaux formation of erythrocytes. However, the present inventors have found that it is difficult to evaluate rouleaux formation when the values of electrical characteristics are used as they are. Hence, the temporal change data of the electrical characteristics of the blood sample is corrected by the electrical measurement data correlating with the hematocrit value and/or the hemoglobin amount; thereby, a value correlating with the erythrocyte sedimentation rate (ESR) measured by a common conventional method has been successfully obtained and the present technology has been completed.

Specific frequencies for the temporal change data of the electrical characteristics of the blood sample which can be used in the blood condition analyzing device 1 according to the second embodiment are not particularly limited to the extent that the effect of the present technology is not impaired. In the present technology, it is particularly preferable to use the temporal change data of the electrical characteristics of the blood sample at a frequency of 100 kHz to 40 MHz. This is because the value obtained by correcting the temporal change data of electrical characteristics in this frequency range by electrical measurement data correlating with the hematocrit value and/or the hemoglobin amount has a high correlation with the erythrocyte sedimentation rate (ESR) measured by a common conventional method.

The electrical measurement data correlating with the hematocrit value and/or the hemoglobin amount used to perform correction in the blood condition analyzing device 1 according to the second embodiment are the same as the electrical characteristics used in the first embodiment described above, and a description is omitted herein.

The reference character C in FIG. 1 is a schematic conceptual diagram schematically showing the concept of a third embodiment of the blood condition analyzing device 1 according to the present technology. The third embodiment is a configuration in which the erythrocyte quantitative evaluation unit 11 and the blood rouleaux evaluation unit 12 are provided in the same device. In the blood condition analyzing device 1 according to the present technology, by both of the erythrocyte quantitative evaluation unit 11 and the blood rouleaux evaluation unit 12 being included, while the hematocrit value and/or the hemoglobin amount is evaluated on the basis of electrical measurement data correlating with the hematocrit value and/or the hemoglobin amount, the rouleaux formation of erythrocytes can be evaluated simultaneously by correcting the temporal change data using the electrical measurement data.

(3) Erythrocyte Sedimentation Evaluation Unit 13

The reference character D in FIG. 1 is a schematic conceptual diagram schematically showing the concept of a fourth embodiment of the blood condition analyzing device 1 according to the present technology. The fourth embodiment is a configuration in which the blood rouleaux evaluation unit 12 and the erythrocyte sedimentation evaluation unit 13 are provided in the same device. In the erythrocyte sedimentation evaluation unit 13, the degree of erythrocyte sedimentation is evaluated on the basis of the rouleaux formation evaluation evaluated by the blood rouleaux evaluation unit 12 mentioned above. The erythrocyte sedimentation evaluation unit 13 is not essential in the blood condition analyzing device 1 according to the present technology, and it is also possible to evaluate the degree of erythrocyte sedimentation using, for example, an electronic computer or the like outside the device on the basis of, for example, the rouleaux formation evaluation evaluated in the blood rouleaux evaluation unit 12 mentioned above.

As described above, the present inventors have found that the rouleaux evaluation value calculated in the blood rouleaux evaluation unit 12 mentioned above has a high correlation with the erythrocyte sedimentation rate (ESR). Therefore, by providing the erythrocyte sedimentation evaluation unit 13 in the blood condition analyzing device 1 according to the present technology, the erythrocyte sedimentation rate (ESR) can be found earlier in a stage before erythrocyte sedimentation occurs.

(4) Blood Coagulation Evaluation Unit 14

The reference character E in FIG. 1 is a schematic conceptual diagram schematically showing the concept of a fifth embodiment of the blood condition analyzing device 1 according to the present technology. The fifth embodiment is a configuration in which the erythrocyte quantitative evaluation unit 11, the blood rouleaux evaluation unit 12, the erythrocyte sedimentation evaluation unit 13, the blood coagulation evaluation unit 14, and the measuring unit 15 are provided in the same device. In the blood coagulation evaluation unit 14, the degree of blood coagulation is evaluated on the basis of the electrical characteristics of a blood sample. The blood coagulation evaluation unit 14 is not essential in the blood condition analyzing device 1 according to the present technology, and it is also possible to evaluate the degree of blood coagulation using, for example, an electronic computer or the like outside the device on the basis of, for example, the electrical characteristics of the blood sample used in the erythrocyte quantitative evaluation unit 11 mentioned above.

In the blood coagulation evaluation unit 14 of the blood condition analyzing device 1 according to the present technology, as described above, one or more known technologies that obtain information on blood coagulation from electrical characteristics such as dielectric constant may be freely selected for use.

By providing the blood coagulation evaluation unit 14 in the blood condition analyzing device 1 according to the present technology, in addition to the evaluation of the hematocrit value and the hemoglobin amount and the evaluation of rouleaux formation and erythrocyte sedimentation, the degree of blood coagulation can be analyzed from the measured electrical characteristics simultaneously in one device. Consequently, a plurality of important blood test results can be obtained by one measurement, and reduction of costs, shortening of the test time, etc. can be achieved.

(5) Measuring Unit 15

In the measuring unit 15, the electrical characteristics of blood at an arbitrary frequency are measured over time. In the blood condition analyzing device 1 according to the present technology, the measuring unit 15 is not essential, and it is also possible to use data measured using an external electrical characteristic measuring device.

The measuring unit 15 may include one or a plurality of blood sample holding units. In the blood condition analyzing device 1, the blood sample holding unit is not essential, and the measuring unit 15 may be designed to be a configuration in which a known cartridge-type container for measurement or the like can be installed, for example.

In the case where the measuring unit 15 includes a blood sample holding unit, the configuration of the blood sample holding unit is not particularly limited to the extent that the blood sample of the measuring object can be held in the measuring unit 15, and may be designed to be an arbitrary configuration. For example, one or a plurality of cells provided on a substrate may be allowed to function as the blood sample holding unit, or one or a plurality of containers may be allowed to function as the blood sample holding unit.

In the case where one or a plurality of containers are used as the blood sample holding unit, the configuration of the container is not particularly limited, and may be freely designed in accordance with the condition, measuring method, etc. of the blood sample to the extent that the blood sample of the measuring object can be held, including a circular cylindrical body, a polygonal cylindrical body with a polygonal cross section (triangle, quadrangle, or polygon with more angles), a conical body, a polygonal pyramid-like body with a polygonal cross section (triangle, quadrangle, or polygon with more angles), or a configuration in which one or more of these are combined.

Also the material that forms the container is not particularly limited, and may be freely selected to the extent that there is no influence on the condition, measurement objective, etc. of the blood sample of the measuring object. In the present technology, in particular, the container is preferably formed using a resin from the viewpoint of the ease of processing and molding etc. In the present technology, also the type of usable resin is not particularly limited, and one or more types of resin usable for the holding of the blood sample may be freely selected for use. For example, a hydrophobic and insulating polymer such as polypropylene, poly(methyl methacrylate), polystyrene, an acrylic, a polysulfone, and polytetrafluoroethylene, a copolymer and a blend polymer thereof, and the like are given. In the present technology, the blood sample holding unit is preferably formed of, among the above materials, particularly one or more types of resin selected from polypropylene, polystyrene, an acrylic, and a polysulfone, because these resins have the property of being low coagulation-active against blood.

The blood sample holding unit is preferably in a configuration capable of being sealed in the state of holding the blood sample. However, the blood sample holding unit may not be in an airtight configuration to the extent that it is capable of being stationary through the time expected to measure the electrical characteristics of the blood sample and there is no influence on measurement.

Specific methods for introducing the blood sample into the blood sample holding unit and for making sealing are not particularly limited, and the introduction may be made by an arbitrary method in accordance with the configuration of the blood sample holding unit. For example, a method in which the blood sample holding unit is provided with a lid, and a blood sample is introduced using a pipette or the like and then the lid is closed to make sealing, a method in which the blood sample holding unit is pierced with a needle from its outer surface, and a blood sample is injected and then the portion pierced with the needle is sealed with grease or the like to make sealing, etc. are given.

The measuring unit 15 may include one or a plurality of applying units. In the blood condition analyzing device 1, the applying unit is not essential, and it is also possible to use an external applying unit by, for example, designing so that an electrode can be inserted into the blood sample holding unit from the outside.

The applying unit applies a prescribed voltage to the blood sample at each set measuring interval from, as the starting time point, the time point at which an order to start measurement is received or the time point at which the power supply for the blood condition analyzing device 1 is set to ON.

The number of electrodes used as part of the applying unit and the material that forms the electrode are not particularly limited to the extent that the effect of the present technology is not impaired, and it is possible to form an arbitrary number of electrodes using an arbitrary material. For example, titanium, aluminum, stainless steel, platinum, gold, copper, graphite, and the like are given. In the present technology, the electrodes are preferably formed of, among the above materials, particularly an electrically conductive material containing titanium, because titanium has the property of being low coagulation-active against blood.

In the measuring unit 15, it is also possible to perform a plurality of measurements. As the method for performing a plurality of measurements, for example, a method in which a plurality of measurements are performed simultaneously by a plurality of measuring units 15 being provided, a method in which a plurality of measurements are performed by scanning one measuring unit 15, a method in which a plurality of measurements are performed by moving the blood sample holding unit, a method in which a plurality of measuring units 15 are provided and switching is performed to select one or a plurality of measuring units 15 that actually perform measurement, etc. may be given.

(6) Storage Unit 16

The blood condition analyzing device 1 according to the present technology may include the storage unit 16 that stores the evaluation results in the erythrocyte quantitative evaluation unit 11, the blood rouleaux evaluation unit 12, the erythrocyte sedimentation evaluation unit 13, and the blood coagulation evaluation unit 14 and the measurement results in the measuring unit 15. In the blood condition analyzing device 1 according to the present technology, the storage unit 16 is not essential, and the results may be stored by connecting an external storage device.

In the blood condition analyzing device 1 according to the present technology, the storage unit 16 may be provided separately for each evaluation unit and the measuring unit, or it is also possible to design so that the results in the evaluation units and the measuring unit are stored in one storage unit 16.

(7) Blood Sample

In the blood condition analyzing device 1 according to the present technology, the blood sample that can be the measuring object is not particularly limited to the extent that it is a sample containing blood, and may be freely selected. Specific examples of the blood sample include a sample containing a blood component such as whole blood, blood plasma, or a diluted solution and/or a drug-added substance thereof, etc.

2. Blood Condition Analyzing system 10

Figure 2:
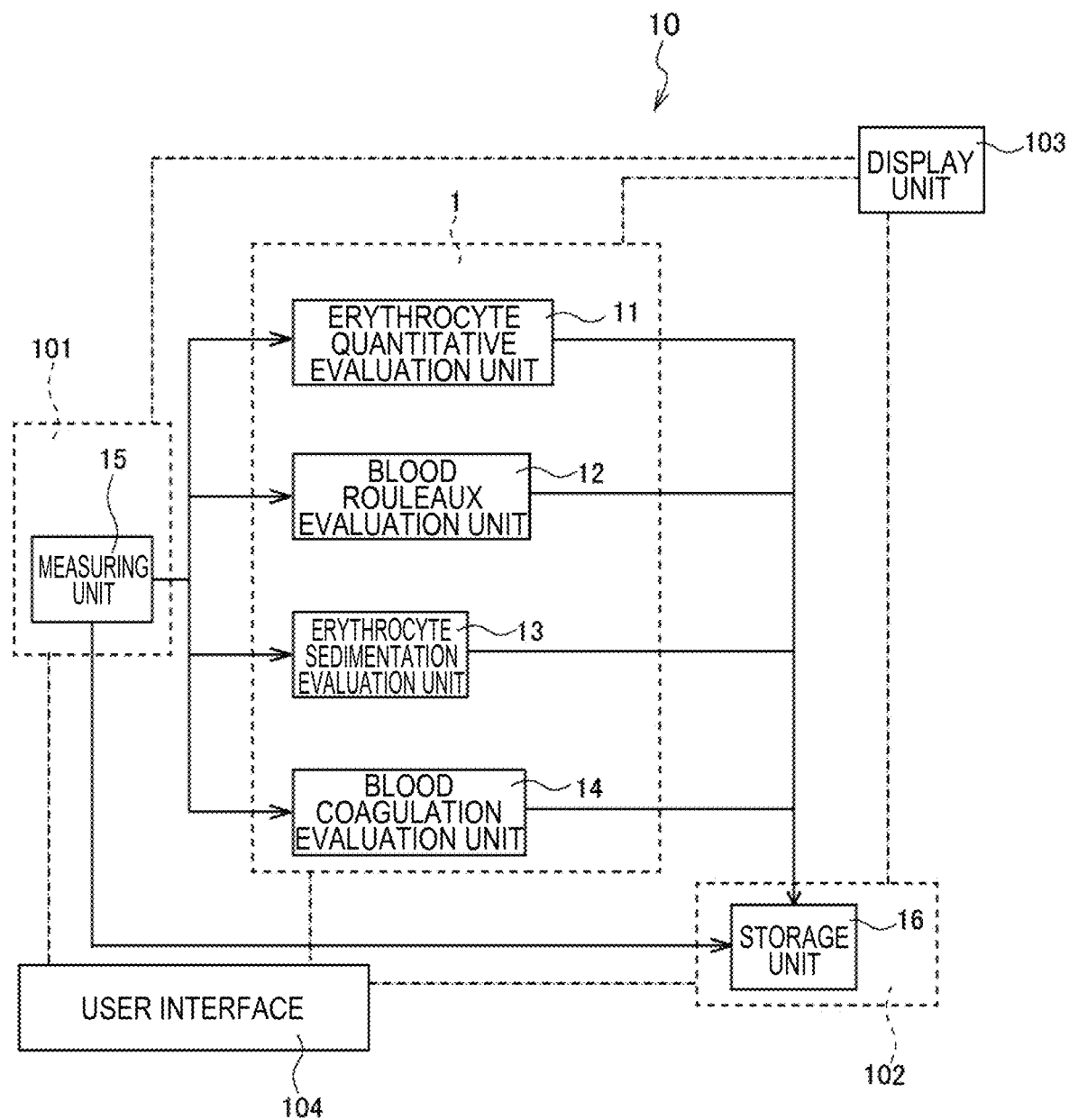
FIG. 2 is a schematic conceptual diagram schematically showing the concept of a blood condition analyzing system 10 according to the present technology.

FIG. 2 is a schematic conceptual diagram schematically showing the concept of a blood condition analyzing system 10 according to the present technology. The blood condition analyzing system 10 according to the present technology includes, in terms of broad categories, at least an electrical characteristic measuring device 101 and the blood condition analyzing device 1. The blood condition analyzing system 10 may include, as necessary, a server 102, a display unit 103, a user interface 104, etc. Each component will now be described in detail.

(1) Electrical Characteristic Measuring Device 101

The electrical characteristic measuring device 101 includes the measuring unit 15 that measures the electrical characteristics of blood at an arbitrary frequency over time. The details of the measuring unit 15 are the same as those of the measuring unit 15 in the blood condition analyzing device 1 described above.

(2) Blood Condition Analyzing Device 1

The blood condition analyzing device 1 includes at least the erythrocyte quantitative evaluation unit 11 or the blood rouleaux evaluation unit 12. The blood condition analyzing device 1 may include, as necessary, the erythrocyte sedimentation evaluation unit 13, the blood coagulation evaluation unit 14, etc. Each component included in the blood condition analyzing device 1 is the same as the details of the blood condition analyzing device 1 described above.

(3) Server 102

The server 102 includes a storage unit 16 that stores the measurement results in the electrical characteristic measuring device 101 and/or the analysis results in the blood condition analyzing device 1. The details of the storage unit 16 are the same as those of the storage unit 16 in the blood condition analyzing device 1 described above.

(4) Display Unit 103

On the display unit 103, the evaluation results in the erythrocyte quantitative evaluation unit 11, the blood rouleaux evaluation unit 12, the erythrocyte sedimentation evaluation unit 13, and the blood coagulation evaluation unit 14, the measurement results in the measuring unit 15, etc. are displayed. It is possible to provide a plurality of display units 103 individually for data or results to be displayed, or to display all data or results on one display unit 103.

(5) User Interface 104

The user interface 104 is a part for a user's operation. A user can access each part of the blood condition analyzing system 10 according to the present technology through the user interface 104.

In the blood condition analyzing system 10 according to the present technology described above, the electrical characteristic measuring device 101, the blood condition analyzing device 1, the server 102, the display unit 103, and the user interface 104 may be connected to each other via a network.

3. Blood Condition Analyzing Method

Figure 3:
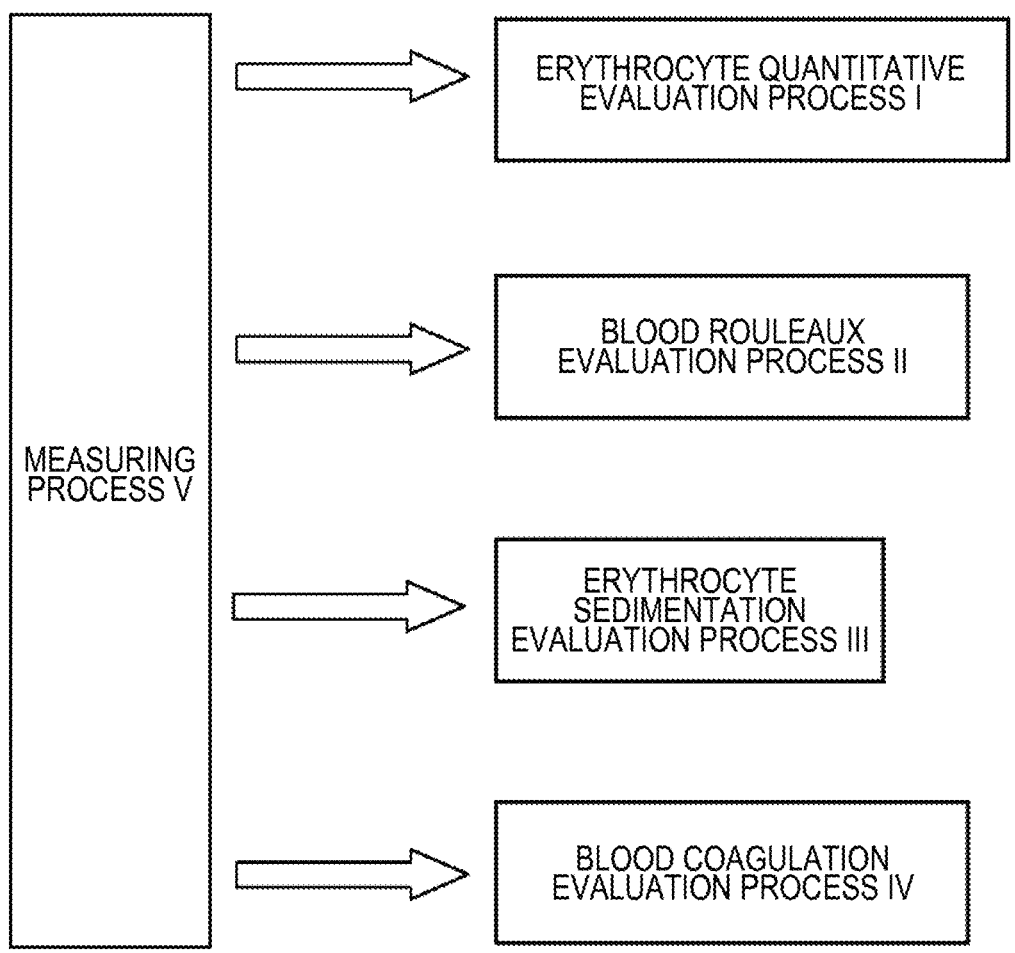
FIG. 3 is a flow chart of a blood condition analyzing method according to the present technology.
Figure 10:
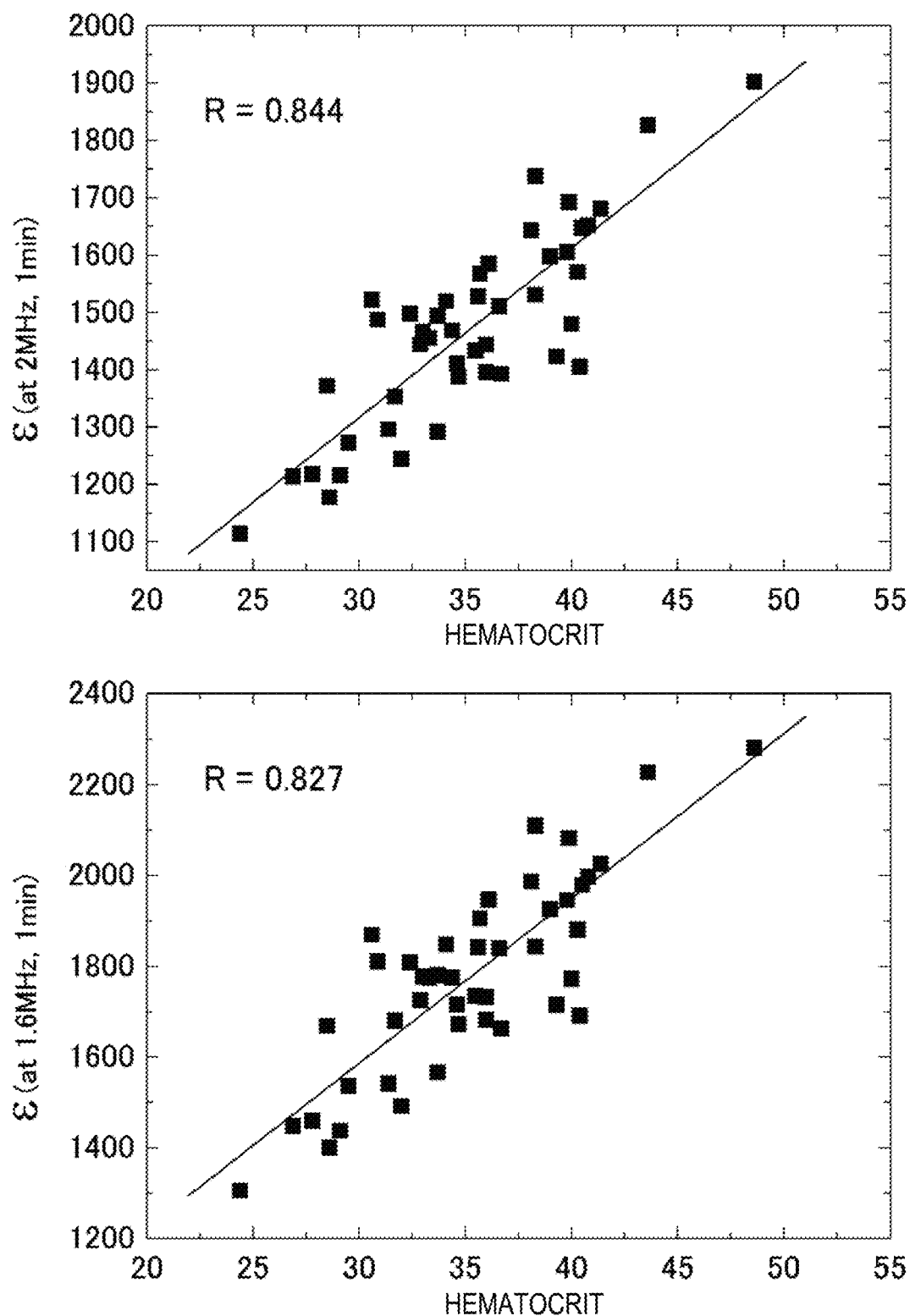
FIG. 10 is drawing-substitute graphs showing the relationship between the dielectric constant and the hematocrit value at each frequency found in Example 1.

FIG. 3 is a flow chart of a blood condition analyzing method according to the present technology. In the blood condition analyzing method according to the present technology, an erythrocyte quantitative evaluation process I and/or a blood rouleaux evaluation process II is performed. It is also possible to perform an erythrocyte sedimentation evaluation process III, a blood coagulation evaluation process IV, a measuring process V, etc., as necessary. Each process will now be described in detail.

(1) Erythrocyte Quantitative Evaluation Process I

The erythrocyte quantitative evaluation process I is a process that evaluates the hematocrit value and/or the hemoglobin amount on the basis of the electrical characteristics of a blood sample at a frequency of 2 to 25 MHz. The details of the evaluation method performed in the erythrocyte quantitative evaluation process I are the same as those of the evaluation method performed in the erythrocyte quantitative evaluation unit 11 of the blood condition analyzing device 1 described above.

(2) Blood Rouleaux Evaluation Process II

The blood rouleaux evaluation process II is a process that evaluates the rouleaux formation of erythrocytes by dividing the temporal change data of the electrical characteristics of a blood sample at a prescribed frequency by the electrical measurement data of the blood sample at a frequency of 2 to 25 MHz. The details of the evaluation method performed in the blood rouleaux evaluation process II are the same as those of the evaluation method performed in the blood rouleaux evaluation unit 12 of the blood condition analyzing device 1 described above.

(3) Erythrocyte Sedimentation Evaluation Process III

The erythrocyte sedimentation evaluation process III is a process that evaluates the degree of erythrocyte sedimentation on the basis of the rouleaux formation evaluation evaluated in the blood rouleaux evaluation process II mentioned above. The details of the evaluation method performed in the erythrocyte sedimentation evaluation process III are the same as those of the evaluation method performed in the erythrocyte sedimentation evaluation unit 13 of the blood condition analyzing device 1 described above.

(4) Blood Coagulation Evaluation Process IV

The blood coagulation evaluation process IV is a process that evaluates the degree of blood coagulation on the basis of the electrical characteristics of a blood sample. The details of the evaluation method performed in the blood coagulation evaluation process IV are the same as those of the evaluation method performed in the blood coagulation evaluation unit 14 of the blood condition analyzing device 1 described above.

(5) Measuring Process V

The measuring process V is a process that measures the electrical characteristics of blood at an arbitrary frequency over time. In the blood condition analyzing method according to the present technology, the measuring process V is not an essential process, and it is also possible to perform analysis using data measured beforehand. The details of the measuring method performed in the measuring process V are the same as those of the measuring method performed in the measuring unit 15 of the blood condition analyzing device 1 described above.

4. Blood Condition Analyzing Program

A blood condition analyzing program according to the present technology is a program for causing a computer to execute an erythrocyte quantitative evaluation function and/or a blood rouleaux evaluation function. It is also possible to cause a computer to execute a erythrocyte sedimentation evaluation function, a blood coagulation evaluation function, etc., as necessary.

In other words, the blood condition analyzing program according to the present technology is a program for causing a computer to execute the blood condition analyzing method according to the present technology described above. Thus, the details of each function are the same as those of each process of the blood condition analyzing method described above, and a description is omitted herein.

Example 1

In Example 1, the correlation between the electrical characteristics and the hematocrit value of a blood sample was investigated. In the Example, dielectric constant was used as an example of the electrical characteristics of the blood sample.

[Experimental Method]

(1) Measurement of Electrical Characteristics

A blood sample collected using a vacuum blood collection tube in which sodium citrate was put as an anticoagulant was kept warm at 37° C. beforehand, and immediately before the start of measurement, a 0.25 M calcium chloride aqueous solution was added at a concentration of 85 μL to 1 mL of blood; thus, a blood coagulation reaction was started. One minute after the start of the blood coagulation reaction, dielectric constant measurement was performed on the blood sample at a temperature of 37° C. in a frequency range of 1 MHz to 40 MHz.

(2) Measurement of the Hematocrit Value

For the blood sample used in the measurement of electrical characteristics mentioned above, the hematocrit value was measured using a common conventional method.

[Results]

Figure 12:
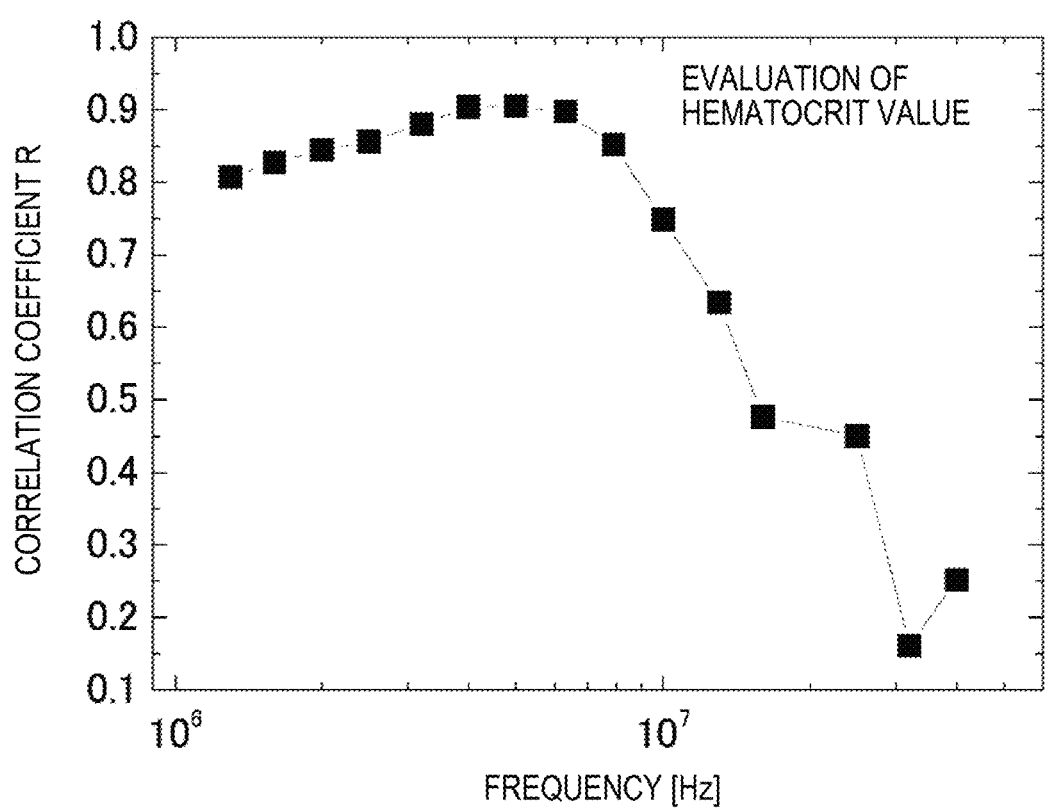
FIG. 12 is a drawing-substitute graph showing the correlation coefficient between the dielectric constant and the hematocrit value at each frequency found in Example 1.
Figure 19:
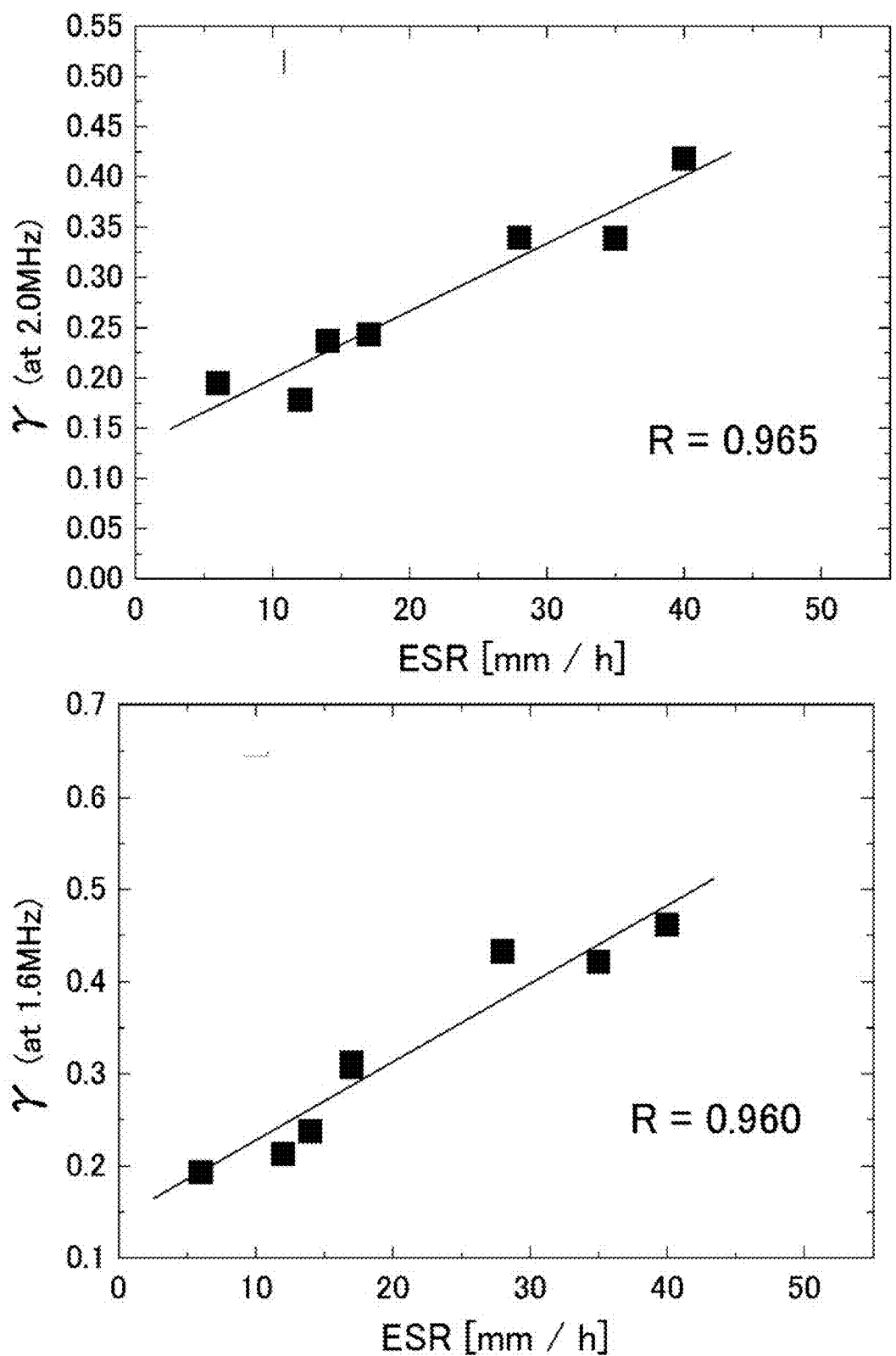
FIG. 19 is drawing-substitute graphs showing the relationship between the blood rouleaux evaluation value ($\gamma$) and the erythrocyte sedimentation rate (ESR) at each frequency found in Example 2.
Figure 27:
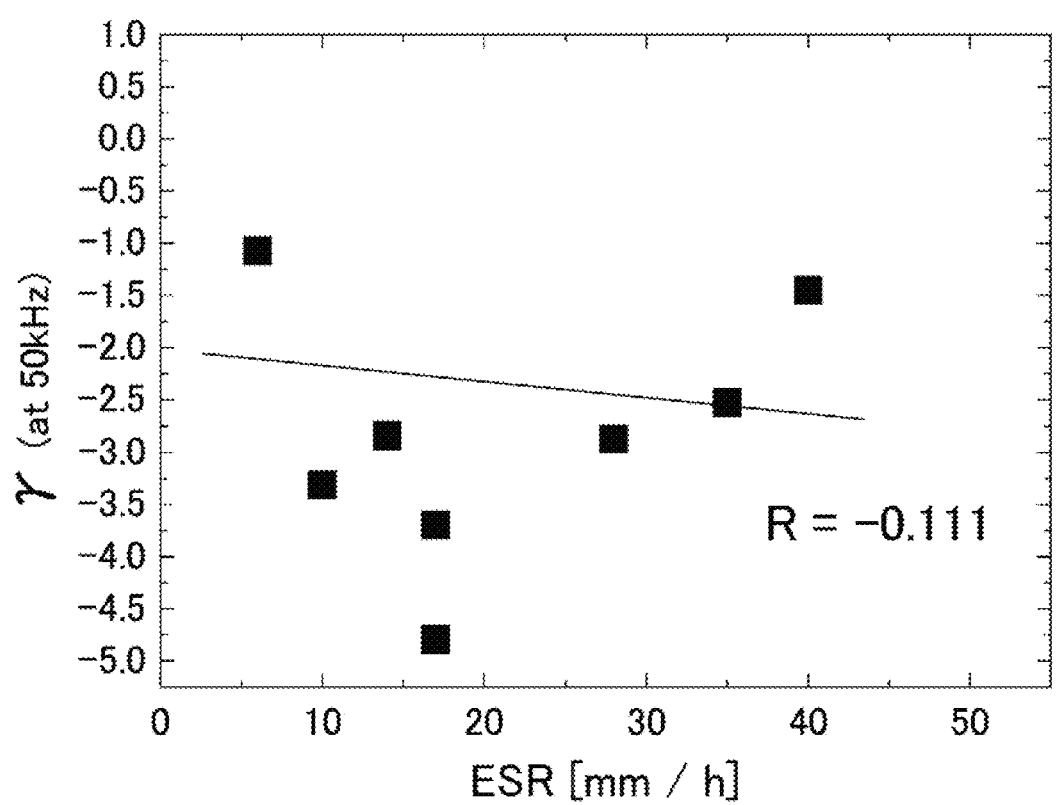
FIG. 27 is drawing-substitute graphs showing the relationship between the blood rouleaux evaluation value ($\gamma$) and the erythrocyte sedimentation rate (ESR) at each frequency found in Example 2.

The relationship between the dielectric constant and the hematocrit value at each frequency is shown in drawing-substitute graphs of FIGS. 4 to 11. Each correlation coefficient between the dielectric constant and the hematocrit value at each frequency is shown in Table 2 below and FIG. 12.

TABLE 2

| Frequency | Correlation coefficient between dielectric constant and hematocrit value |
|---|---|
| 40 MHz | 0.252 |
| 32 MHz | 0.161 |
| 25 MHz | 0.450 |
| 16 MHz | 0.476 |
| 13 MHz | 0.634 |
| 10 MHz | 0.748 |
| 7.9 MHz | 0.852 |
| 6.3 MHz | 0.897 |
| 5.0 MHz | 0.905 |
| 4.0 MHz | 0.904 |
| 3.2 MHz | 0.880 |
| 2.5 MHz | 0.856 |
| 2.0 MHz | 0.844 |
| 1.6 MHz | 0.827 |
| 1.3 MHz | 0.807 |
| 1.0 MHz | 0.804 |

As shown in Table 2, it has been found that the correlation coefficient decreases rapidly at 32 MHz or more. Although also the correlation coefficients at 10 MHz to 25 Mhz are not so high, this is because at high frequencies the electrical response by the erythrocyte will be feeble and therefore susceptible to noise; and if a higher precision measuring device is used, these correlation coefficients are expected to be higher. On the other hand, it has been found that the correlation coefficient is generally high at low frequencies and it is in the case of 5 MHz that the maximum value is reached. However, with proximity to 1 MHz, it becomes more likely to receive the influence of erythrocyte rouleaux as described above. The influence will be greater particularly when the time from the mixing of the calcium aqueous solution to the start of measurement is not accurate. That is, it is presumed that, as the frequency decreases (comes closer to 1 MHz), stable analysis becomes more difficult because the dielectric constant varies greatly with time even immediately after the start of measurement. In view of these matters, it has been concluded that the hematocrit value can be evaluated with high precision when the electrical characteristics of the blood sample at a frequency of 2 to 25 MHz are used.

Since also the hemoglobin amount is a quantitative measurement value of erythrocytes similarly to the hematocrit value, it is presumed that the electrical characteristics of the blood sample at a frequency of 2 to 25 MHz correlate also with the hemoglobin amount. That is, it is suggested that also the hemoglobin amount can be evaluated with high precision when the electrical characteristics of the blood sample at a frequency of 2 to 25 MHz are used.

Example 2

In Example 2, the correlation between the blood rouleaux evaluation value calculated in the blood rouleaux evaluation unit 12 of the blood condition analyzing device 1 according to the present technology and the erythrocyte sedimentation rate (ESR) was investigate. In the Example, dielectric constant was used as an example of the electrical characteristics of the blood sample.

[Experimental Method]

(1) Measurement of Electrical Characteristics

A blood sample collected using a vacuum blood collection tube in which sodium citrate was put as an anticoagulant was kept warm at 37° C. beforehand, and immediately before the start of measurement, a 0.25 M calcium chloride aqueous solution was added at a concentration of 85 μL to 1 mL of blood; thus, a blood coagulation reaction was started. From one minute after the start of the blood coagulation reaction, dielectric constant measurement was performed on the blood sample at a temperature of 37° C. in a frequency range of 50 kHz to 40 MHz at measuring intervals of one minute.

(2) Calculation of the Blood Rouleaux Evaluation Value

The difference between the electrical characteristic (dielectric constant) of the blood sample at a time when rouleaux have proceeded and the electrical characteristic (dielectric constant) of the blood sample before rouleaux proceed was divided by the electrical measurement data of the blood sample at a frequency of 6.3 MHz; thereby, the blood rouleaux evaluation value ($\gamma$) was calculated. The dielectric constant after 10 minutes was used as the electrical characteristic (dielectric constant) of the blood sample at a time when rouleaux have proceeded, and the average of the dielectric constants after 2 minutes and after 3 minutes was used as the electrical characteristic (dielectric constant) of the blood sample before rouleaux proceed.

(3) Measurement of the Erythrocyte Sedimentation Rate (ESR)

For the blood sample used in the measurement of electrical characteristics mentioned above, the erythrocyte sedimentation rate (ESR) was measured using a common conventional method.

[Results]

Figure 28:
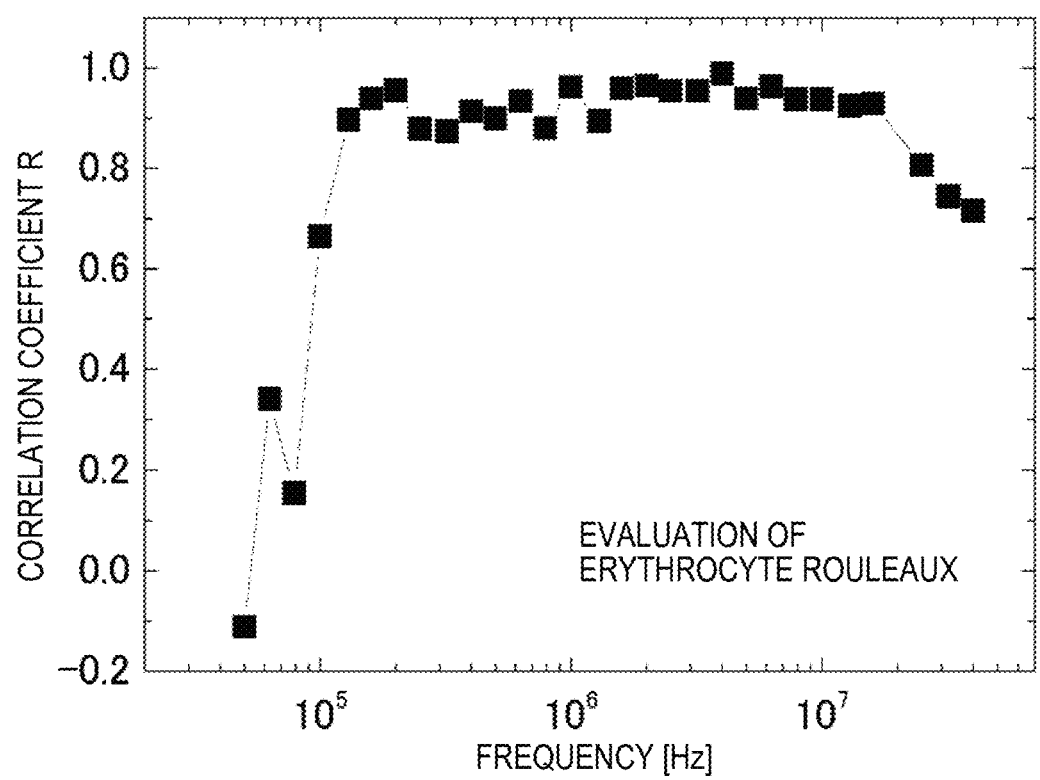
FIG. 28 is a drawing-substitute graph showing the correlation coefficient between the blood rouleaux evaluation value ($\gamma$) and the erythrocyte sedimentation rate (ESR) at each frequency found in Example 2.

The relationship between the blood rouleaux evaluation value ($\gamma$) and the erythrocyte sedimentation rate (ESR) at each frequency is shown in drawing-substitute graphs of FIGS. 13 to 27. Each correlation coefficient between the blood rouleaux evaluation value ($\gamma$) and the erythrocyte sedimentation rate (ESR) at each frequency is shown in Table 3 below and FIG. 28.

TABLE 3

| Frequency | Correlation coefficient between $\gamma$ and ESR |
|---|---|
| 40 MHZ | 0.716 |
| 32 MHz | 0.745 |
| 25 MHz | 0.806 |
| 16 MHz | 0.929 |
| 13 MHz | 0.925 |
| 10 MHz | 0.938 |
| 7.9 MHz | 0.938 |
| 6.3 MHz | 0.964 |
| 5.0 MHz | 0.940 |
| 4.0 MHz | 0.989 |
| 3.2 MHz | 0.954 |
| 2.5 MHz | 0.955 |
| 2.0 MHz | 0.965 |
| 1.6 MHz | 0.960 |

TABLE 3-continued

| Frequency | Correlation coefficient between γ and ESR |
|---|---|
| 1.3 MHz | 0.895 |
| 1.0 MHz | 0.963 |
| 790 kHz | 0.881 |
| 630 kHz | 0.934 |
| 500 kHz | 0.900 |
| 400 kHz | 0.914 |
| 320 kHz | 0.874 |
| 250 kHz | 0.880 |
| 200 kHz | 0.956 |
| 160 kHz | 0.939 |
| 130 kHz | 0.897 |
| 100 kHz | 0.665 |
| 79 kHz | 0.155 |
| 63 kHz | 0.340 |
| 50 kHz | −0.111 |

As shown in Table 3, it has been found that the blood rouleaux evaluation value (γ) and the erythrocyte sedimentation rate (ESR) correlate highly at frequencies of 100 kHz to 40 MHz. In particular, it has been found that in the high frequency range of 10 MHz or more, the correlation coefficient between the blood rouleaux evaluation value (γ) and the erythrocyte sedimentation rate (ESR) is high although the amount of change in dielectric constant due to erythrocyte rouleaux is small. From these results, it has been found that the function system of Mathematical Formula (3) above is a good function system capable of evaluating the influence of erythrocyte rouleaux with good precision from a small amount of change in a high frequency range due to erythrocyte rouleaux.

INDUSTRIAL APPLICABILITY

According to the present technology, the evaluation of the hematocrit value and the hemoglobin amount and the degree of rouleaux formation, erythrocyte sedimentation, and blood coagulation can be analyzed simultaneously from the electrical characteristics of a blood sample measured. Consequently, a plurality of important blood test results can be obtained by one measurement, and reduction of costs, shortening of the test time, etc. can be achieved.

Erythrocyte sedimentation and blood coagulation are influenced by various factors such as fibrinogen. Therefore, if measurement can be performed for various conditions of blood simultaneously, each measured value can be used for the correction of each analysis, and this can contribute to construction of high diagnostic technique.

Additionally, the present technology may also be configured as below.

(1)

A blood condition analyzing device including:

an erythrocyte quantitative evaluation unit configured to evaluate a hematocrit value and/or a hemoglobin amount on the basis of an electrical characteristic of a blood sample at a frequency of 2 to 25 MHz.

(2)

A blood condition analyzing device including:

a blood rouleaux evaluation unit configured to evaluate rouleaux formation of erythrocytes by dividing temporal change data of an electrical characteristic of a blood sample at a prescribed frequency by electrical measurement data of the blood sample at a frequency of 2 to 25 MHz.

(3)

The blood condition analyzing device according to (2), wherein the temporal change data of the electrical characteristic is a difference between an electrical characteristic of the blood sample at a time when rouleaux have proceeded and an electrical characteristic of the blood sample before rouleaux proceed.

(4)

The blood condition analyzing device according to (2) or (3), wherein the temporal change data of the electrical characteristic is temporal change data of the electrical characteristic of the blood sample at a frequency of 100 kHz to 40 MHz.

(5)

The blood condition analyzing device according to any one of (2) to (4), further including:

an erythrocyte sedimentation evaluation unit configured to evaluate a degree of erythrocyte sedimentation on the basis of rouleaux formation evaluation evaluated by the blood rouleaux evaluation unit.

(6)

The blood condition analyzing device according to any one of (2) to (5), further including:

an erythrocyte quantitative evaluation unit configured to evaluate a hematocrit value and/or a hemoglobin amount on the basis of an electrical characteristic of a blood sample at a frequency of 2 to 25 MHz.

(7)

The blood condition analyzing device according to any one of (1) to (6), further including:

a blood coagulation evaluation unit configured to evaluate a degree of blood coagulation on the basis of an electrical characteristic of a blood sample.

(8)

The blood condition analyzing device according to (1) to (7), further including:

a measuring unit configured to measure an electrical characteristic of a blood sample over time.

(9)

A blood condition analyzing system including:

an electrical characteristic measuring device including a measuring unit configured to measure an electrical characteristic of blood over time; and a blood condition analyzing device including an erythrocyte quantitative evaluation unit configured to evaluate a hematocrit value and/or a hemoglobin amount on the basis of an electrical characteristic of a blood sample at a frequency of 2 to 25 MHz.

(10)

A blood condition analyzing system including:

an electrical characteristic measuring device including a measuring unit configured to measure an electrical characteristic of blood over time; and a blood condition analyzing device including a blood rouleaux evaluation unit configured to evaluate rouleaux formation of erythrocytes by dividing temporal change data of an electrical characteristic of a blood sample at a prescribed frequency by electrical measurement data of the blood sample at a frequency of 2 to 25 MHz.

(11)

The blood condition analyzing system according to (9) or (10), further including:

a server including an information storage unit configured to store a measurement result in the electrical characteristic measuring device and/or an analysis result in the blood condition analyzing device.

(12)
The blood condition analyzing system according to (11), wherein the server is connected to the electrical characteristic measuring device and/or the blood condition analyzing device via a network.

(13)
A blood condition analyzing method including:
an erythrocyte quantitative evaluation process of evaluating a hematocrit value and/or a hemoglobin amount on the basis of an electrical characteristic of a blood sample at a frequency of 2 to 25 MHz.

(14)
A blood condition analyzing method including:
a blood rouleaux evaluation process of evaluating rouleaux formation of erythrocytes by dividing temporal change data of an electrical characteristic of a blood sample at a prescribed frequency by electrical measurement data of the blood sample at a frequency of 2 to 25 MHz.

(15)
A blood condition analyzing program for causing a computer to execute:
an erythrocyte quantitative evaluation function of evaluating a hematocrit value and/or a hemoglobin amount on the basis of an electrical characteristic of a blood sample at a frequency of 2 to 25 MHz.

(16)
A blood condition analyzing program for causing a computer to execute:
a blood rouleaux evaluation function of evaluating rouleaux formation of erythrocytes by dividing temporal change data of an electrical characteristic of a blood sample at a prescribed frequency by electrical measurement data of the blood sample at a frequency of 2 to 25 MHz.

REFERENCE SIGNS LIST 1 blood condition analyzing device
11 erythrocyte quantitative evaluation unit
12 blood rouleaux evaluation unit
13 erythrocyte sedimentation evaluation unit
14 blood coagulation evaluation unit
15 measuring unit
16 storage unit
10 blood condition analyzing system
101 electrical characteristic measuring device
102 server
103 display unit
104 user interface
I erythrocyte quantitative evaluation process
II blood rouleaux evaluation process
III erythrocyte sedimentation evaluation process
IV blood coagulation evaluation process
V measuring process

What is claimed:

1. A blood condition analyzing device comprising:
at least a pair of electrodes configured to measure an electrical characteristic of a blood sample at a frequency of 2 to 25 MHz over time; and
at least one processor, operatively coupled to the at least the pair of electrodes, programmed to:
obtain, from the at least the pair of electrodes, the electrical characteristic of the blood sample at the frequency of 2 to 25 MHz;
determine a hematocrit value and/or a hemoglobin amount on the basis of the electrical characteristic of the blood sample at the frequency of 2 to 25 MHz; and
output the hematocrit value and/or the hemoglobin amount.

2. A blood condition analyzing device comprising:
at least a pair of electrodes configured to:
measure temporal change data of an electrical characteristic of a blood sample at a first frequency over time; and
measure electrical measurement data of the blood sample at a second frequency of 2 to 25 MHz; and
at least one processor, operatively coupled to the at least the pair of electrodes, programmed to:
obtain, from the at least the pair of electrodes, the temporal change data of the electrical characteristic of the blood sample at the first frequency;
obtain, from the at least the pair of electrodes, the electrical measurement data of the blood sample at the second frequency of 2 to 25 MHz; and
determine rouleaux formation of erythrocytes by dividing the temporal change data of the electrical characteristic of the blood sample at the first frequency by the electrical measurement data of the blood sample at the second frequency of 2 to 25 MHz.

3. The blood condition analyzing device according to claim 2, wherein the at least one processor is programmed to determine rouleaux formation of erythrocytes based on the temporal change data of the electrical characteristic that is a difference between an electrical characteristic of the blood sample at a time when rouleaux have proceeded and an electrical characteristic of the blood sample before rouleaux proceed.

4. The blood condition analyzing device according to claim 2, wherein the at least one processor is programmed to determine rouleaux formation of erythrocytes based on the temporal change data of the electrical characteristic of the blood sample at a first frequency of 100 kHz to 40 MHz.

5. The blood condition analyzing device according to claim 2, wherein the at least one processor is programmed to determine a degree of erythrocyte sedimentation on the basis of the determined rouleaux formation.

6. The blood condition analyzing device according to claim 2, wherein the at least one processor is programmed to determine a hematocrit value and/or a hemoglobin amount on the basis of an electrical characteristic of a blood sample at a frequency of 2 to 25 MHz.

7. The blood condition analyzing device according to claim 1, wherein the at least one processor is programmed to determine a degree of blood coagulation on the basis of an electrical characteristic of a blood sample.

8. A blood condition analyzing system comprising:
at least a pair of electrodes configured to measure an electrical characteristic of a blood sample at a frequency of 2 to 25 MHz over time; and
at least one processor, operatively coupled to the at least the pair of electrodes; and
at least one non-transitory storage medium having executable instructions stored thereon, that when executed by the at least one processor, cause the at least one processor to perform a method comprising:
obtaining, from the at least the pair of electrodes, the electrical characteristic of the blood sample at the frequency of 2 to 25 MHz;
determining a hematocrit value and/or a hemoglobin amount on the basis of the electrical characteristic of the blood sample at the frequency of 2 to 25 MHz; and
outputting the hematocrit value and/or the hemoglobin amount.

9. A blood condition analyzing system comprising:
at least a pair of electrodes configured to:
  measure temporal change data of an electrical characteristic of a blood sample at a first frequency over time; and
  measure electrical measurement data of the blood sample at a second frequency of 2 to 25 MHz; and
at least one processor, operatively coupled to the at least the pair of electrodes; and
at least one non-transitory storage medium having executable instructions stored thereon, that when executed by the at least one processor, cause the at least one processor to perform a method comprising:
  obtaining, from the at least the pair of electrodes, the temporal change data of the electrical characteristic of the blood sample at the first frequency;
  obtaining, from the at least the pair of electrodes, the electrical measurement data of the blood sample at the second frequency of 2 to 25 MHz; and
  determining rouleaux formation of erythrocytes by dividing the temporal change data of the electrical characteristic of the blood sample at the first frequency by the electrical measurement data of the blood sample at the second frequency of 2 to 25 MHz.

10. The blood condition analyzing system according to claim 8, further comprising:
a computer-implemented server including information storage circuitry configured to store a measurement result and/or an analysis result in the at least one non-transitory storage medium.

11. The blood condition analyzing system according to claim 10, wherein the computer-implemented server is connected to the at least one processor and/or the at least one non-transitory storage medium via a network.

12. A blood condition analyzing method comprising:
measuring, using at least a pair of electrodes, an electrical characteristic of a blood sample at a frequency of 2 to 25 MHz over time;
determining, using at least one programmed processor operatively coupled to the at least the pair of electrodes, a hematocrit value and/or a hemoglobin amount on the basis of the electrical characteristic of the blood sample at the frequency of 2 to 25 MHz; and
outputting, using the at least one programmed processor, the hematocrit value and/or the hemoglobin amount.

13. A blood condition analyzing method comprising:
measuring, using at least a pair of electrodes, temporal change data of an electrical characteristic of a blood sample at a first frequency over time;
measuring, using the at least the pair of electrodes, electrical measurement data of the blood sample at a second frequency of 2 to 25 MHz; and
determining, using at least one programmed processor operatively coupled to the at least the pair of electrodes, rouleaux formation of erythrocytes by dividing the temporal change data of the electrical characteristic of the blood sample at the first frequency by the electrical measurement data of the blood sample at the second frequency of 2 to 25 MHz.

14. A non-transitory computer readable storage medium having computer executable instructions stored thereon, that when executed by a computer, cause the computer to perform a blood condition analyzing program comprising:
obtaining, from at least a pair of electrodes, an electrical characteristic of a blood sample at a frequency of 2 to 25 MHz over time measured using the at least the pair of electrodes;
determining a hematocrit value and/or a hemoglobin amount on the basis of the electrical characteristic of the blood sample at the frequency of 2 to 25 MHz; and
outputting the hematocrit value and/or the hemoglobin amount.

15. A non-transitory computer readable storage medium having computer executable instructions stored thereon, that when executed by a computer, cause the computer to perform a blood condition analyzing program comprising:
obtaining, from at least a pair of electrodes, temporal change data of an electrical characteristic of a blood sample at a first frequency over time measured using the at least the pair of electrodes;
obtaining, from the at least the pair of electrodes, electrical measurement data of the blood sample at a second frequency of 2 to 25 MHz measured using the at least the pair of electrodes; and
determining rouleaux formation of erythrocytes by dividing the temporal change data of the electrical characteristic of the blood sample at the first frequency by the electrical measurement data of the blood sample at the second frequency of 2 to 25 MHz.

* * * * *